United States Patent [19]

Scholz et al.

[11] Patent Number: 5,687,848

[45] Date of Patent: Nov. 18, 1997

[54] MOISTURE-PROOF RESEALABLE POUCH AND CONTAINER

[75] Inventors: Matthew T. Scholz, Woodbury; Jason L. Edgar, Bloomington, both of Minn.

[73] Assignee: Minnesota Mining and Manufacturing Company, St. Paul, Minn.

[21] Appl. No.: 464,050

[22] Filed: Jun. 5, 1995

Related U.S. Application Data

[60] Division of Ser. No. 186,004, Jan. 24, 1994, Pat. No. 5,505,305, which is a continuation-in-part of Ser. No. 98,617, Jul. 28, 1993, abandoned, which is a continuation-in-part of Ser. No. 964,511, Oct. 21, 1992, abandoned, and a continuation-in-part of Ser. No. 40,624, Mar. 31, 1993, abandoned, Continuation-in-part of Ser. No. 964,511, Oct. 21, 1992, abandoned.

[51] Int. Cl.$^6$ .................................................. A61B 17/06
[52] U.S. Cl. ........................ 206/438; 206/440; 206/494; 383/66
[58] Field of Search ........................... 206/233, 440, 206/494, 438, 818; 383/66; 220/230, 231

[56] References Cited

U.S. PATENT DOCUMENTS

| | | |
|---|---|---|
| Re. 26,488 | 11/1968 | Bull .................................. 222/263 |
| 172,039 | 11/1876 | Lazarevitch . |
| 393,874 | 12/1888 | Wood . |
| 1,123,470 | 1/1915 | Betten . |
| 1,208,701 | 12/1916 | Trenner . |
| 1,671,825 | 5/1928 | Johnson . |
| 1,899,625 | 2/1933 | Metts . |
| 2,017,176 | 10/1935 | Andrews ............................. 229/17 |
| 2,367,417 | 1/1945 | Milem ............................. 206/63.2 |
| 2,446,308 | 8/1948 | Smith ............................. 229/14 |
| 2,633,006 | 3/1953 | Taylor ............................. 62/114 |
| 2,672,257 | 3/1954 | Simmonds ............................. 220/32 |
| 2,798,522 | 7/1957 | Hurt ............................. 150/2.1 |
| 2,999,275 | 9/1961 | Blume, Jr. ............................. 18/55 |
| 3,201,027 | 8/1965 | Meyerhoefer ............................. 229/53 |
| 3,380,646 | 4/1968 | Doyen et al. ............................. 229/57 |
| 3,397,818 | 8/1968 | Rey ............................. 221/232 |
| 3,454,197 | 7/1969 | Thompson ............................. 22/105 |
| 3,575,225 | 4/1971 | Muheim ............................. 150/8 |
| 3,629,905 | 12/1971 | Cote ............................. 24/30.5 R |
| 3,749,301 | 7/1973 | Peckar ............................. 229/44 R |
| 3,795,355 | 3/1974 | Gerstein ............................. 225/106 |
| 3,961,721 | 6/1976 | Gordon et al. ............................. 220/230 |
| 4,033,013 | 7/1977 | Peterson ............................. 24/201 B |
| 4,146,133 | 3/1979 | Bogorad et al. ............................. 206/439 |

(List continued on next page.)

FOREIGN PATENT DOCUMENTS

| | | | |
|---|---|---|---|
| 0 004 396 | 10/1979 | European Pat. Off. ........ | B65D 31/14 |
| 1-167055 | 6/1989 | Japan ............... | B65D 45/02 |
| 1 351 196 | 4/1974 | United Kingdom ........... | B65D 47/08 |

OTHER PUBLICATIONS

3M Data Sheet entitled "Magnet Material B–1033 Preliminary Product Information", Brochure No. 80–6105–6698–8; 3M 1990 (2 pgs).

3M Data Sheet entitled "Scotch™ 1316/1317 Magnet Tape—Pressure–sensitive adhesive, high energy level magnetic material", Brochure No. 80–6105–6671–5; 3M 1990 (2 pgs).

DuPont Brochure entitled "Surlyn® Ionomer Resin—Selector Guide", DuPont Chemical Company, undated (5 pgs).

Sketch of Artic Tote™ picnic cooler having magnetic closure (A M K Designs, Inc.)—Marked as Exhibit A.

*Primary Examiner*—M. D. Patterson
*Attorney, Agent, or Firm*—Gary L. Griswold; Walter N. Kirn; Stephen W. Bauer

[57] ABSTRACT

The present invention relates to an easy-to-use and effective magnetically resealable moisture-proof pouch containing moisture-curable orthopedic splinting/casting product in bulk form or in individually packaged rolls. The preferred pouch incorporates a frame disposed about an opening into the pouch which provides a mounting place for a moisture-proof magnetic seal. Also disclosed are containers for the preferred pouches which are adapted for use with the magnetic sealing system according to the present invention.

22 Claims, 21 Drawing Sheets

U.S. PATENT DOCUMENTS

| | | | |
|---|---|---|---|
| 4,176,746 | 12/1979 | Kooi | 206/438 |
| 4,193,513 | 3/1980 | Bull, Jr. | 222/1 |
| 4,232,721 | 11/1980 | Martin et al. | 150/0.5 |
| 4,269,315 | 5/1981 | Boyce | 206/438 |
| 4,295,565 | 10/1981 | Takeuchi | 206/455 |
| 4,451,321 | 5/1984 | McKelvey | 156/382 |
| 4,598,826 | 7/1986 | Shinbach | 206/620 |
| 4,609,578 | 9/1986 | Reed | 428/76 |
| 4,667,661 | 5/1987 | Scholz et al. | 128/90 |
| 4,672,688 | 6/1987 | Kalkipsakis | 383/58 |
| 4,732,299 | 3/1988 | Hoyt | 222/94 |
| 4,770,229 | 9/1988 | Komori et al. | 164/440 |
| 4,770,299 | 9/1988 | Parker | 206/409 |
| 4,774,937 | 10/1988 | Scholz et al. | 128/90 |
| 4,790,436 | 12/1988 | Nakamura | 206/449 |
| 4,848,575 | 7/1989 | Nakamura et al. | 205/449 |
| 4,869,046 | 9/1989 | Parker | 53/416 |
| 4,899,738 | 2/1990 | Parker | 128/90 |
| 4,903,837 | 2/1990 | Duello | 206/440 |
| 4,968,542 | 11/1990 | Gasper et al. | 428/76 |
| 5,003,970 | 4/1991 | Parker et al. | 128/90 |
| 5,005,707 | 4/1991 | Hustad et al. | 205/532 |
| 5,027,803 | 7/1991 | Scholz et al. | 128/89 R |
| 5,145,091 | 9/1992 | Meyers | 221/45 |
| 5,148,916 | 9/1992 | Tillyer, Sr. | 206/352 |
| 5,178,300 | 1/1993 | Haviv et al. | 222/95 |
| 5,505,305 | 4/1996 | Scholz et al. | 206/438 |

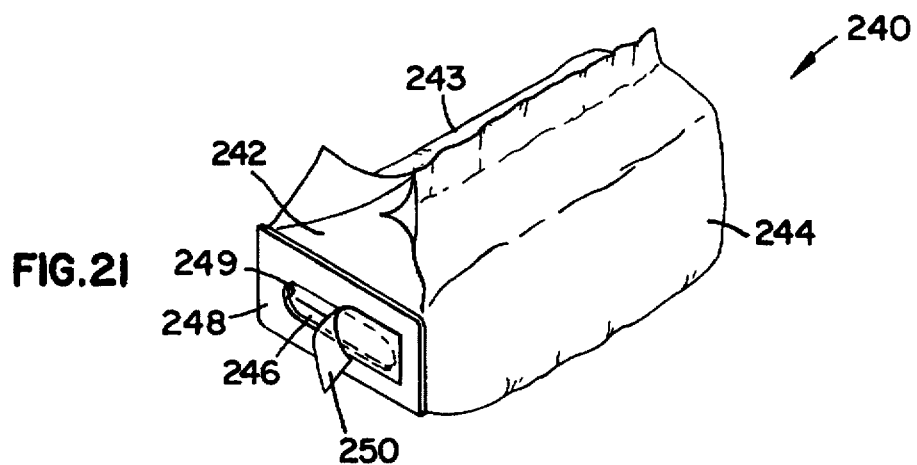
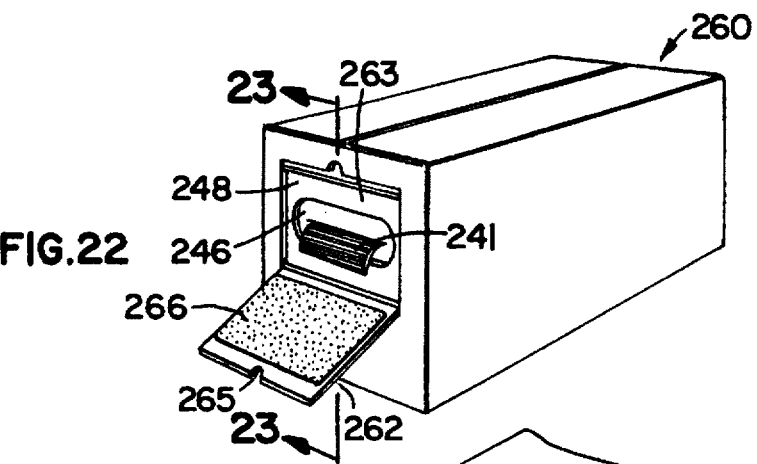
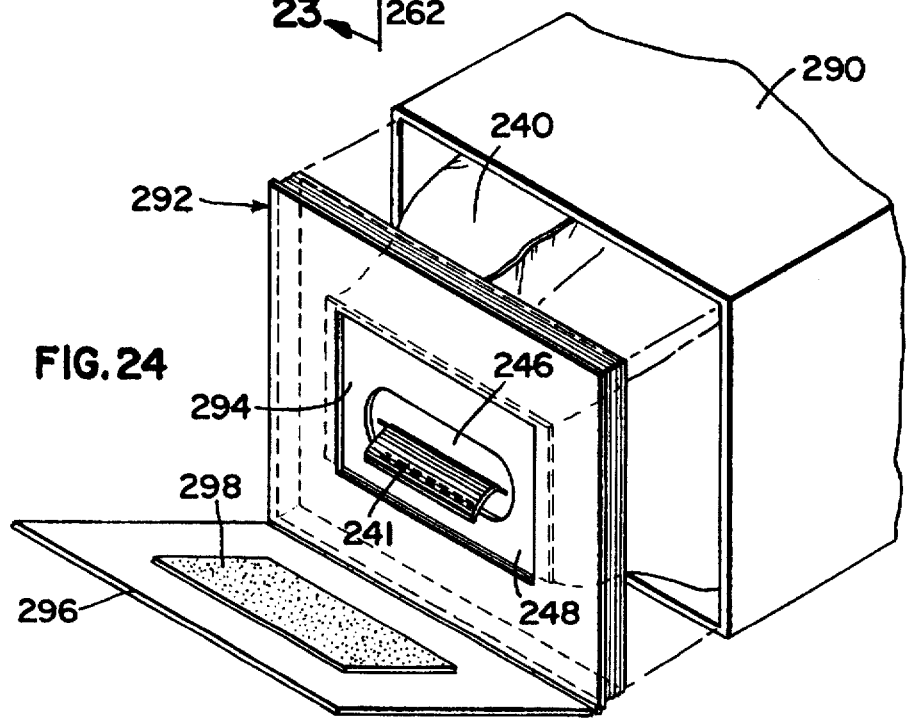

MOISTURE-PROOF RESEALABLE POUCH AND CONTAINER

This is a division of application Ser. No. 08/186,004, filed Jan. 24, 1994, U.S. Pat. No. 5,505,305 which, in turn is a continuation-in-part of U.S. patent application Ser. No. 08/098,617, filed Jul. 28, 1993, abandoned, which is a continuation-in-part of U.S. patent application Ser. No. 07/964,511, filed Oct. 21, 1992, abandoned and U.S. patent application Ser. No. 08/040,624, filed Mar. 31, 1993, abandoned which is a continuation-in-part of U.S. patent application Ser. No. 07/964,511, filed Oct. 21, 1992, abandoned.

FIELD OF THE INVENTION

This invention relates to the field of orthopedic splinting/casting products and more particularly to magnetically resealable moisture-proof pouches and containers for storing and dispensing moisture-curable orthopedic splinting/casting products.

BACKGROUND OF THE INVENTION

The orthopedic immobilization industry has developed a need for a resealable package used with continuous length moisture-curable synthetic splinting materials. Preferred moisture-curable synthetic splinting materials are described in, for example, the following U.S. Pat. Nos.: 4,609,578 to Reed; 4,667,661 to Scholz et al.; 4,774,937 to Scholz et al.; and 5,027,803 to Scholz et al.—all of which are hereby incorporated by reference. These products are typically moisture-curable, i.e., exposure to moisture, including ambient humidity levels, causes these products to rapidly stiffen and form a cured splint or cast.

The requirements for packaging these products include a long shelf life—preferably greater than one year at ambient conditions along with a package allowing easy dispensing of the product. This problem is made more acute because the product is not refrigerated, but is instead typically stored at ambient temperature. For the above reasons, any package for these products preferably forms a hermetic seal which is moisture-impermeable.

Due to the stringent packaging requirements, these products have typically been packaged in single-use packages containing pre-cut lengths of the products. Such packaging, however, sometimes results in wasted product and packaging material as well as the increased costs of individually packaging each pre-cut length of casting/splinting material.

Attempts have been made to package these products in continuous-length packaging to avoid the waste associated with pre-cut length packaging. U.S. Pat. Nos. 4,770,299 to Parker, 4,869,046 to Parker and 4,899,738 to Parker all disclose a medical bandaging product packaged in an outer sleeve of a moisture-impermeable material such as an aluminum foil laminate. The moisture-proof outer sleeve package must be as long as the product contained therein. The products are typically rolled up and placed in a box and then unrolled and cut to length with the packaging material being resealed after each use. This packaging system has the advantage of allowing the product to be cut to the particular length desired, but also has several disadvantages.

Those disadvantages include that packaging the material as a roll in a box produces many creases in the relatively stiff aluminum foil packaging laminate which is typically used for packaging. The creases are a source of pinholes which leak and cause premature curing of the product in the package. Also, because the entire length of the product must be enclosed in an outer wrap of the packaging material, a relatively large amount of packaging material is used which adds to the cost of the product. Finally, the closure systems used with such packaging are cumbersome and ineffective, allowing the product to harden on the end nearest the opening between uses. As a result, the material must be typically cut twice, once to remove the hardened portion and once to cut the desired length of material needed. This adds to waste when the product is stored in the above manner.

One attempt to solve the problems associated with packaging the entire length of the product is disclosed in U.S. Pat. No. 5,003,970 to Parker et al. That patent discloses a continuous length splinting material packaged in an outer container formed of a moisture-impervious material. The bulk of the product is stored in an enlarged area with an elongate dispensing sleeve extending from the enlarged area of the package.

The package appears to include two side panels having an enlarged area and tapering to form the sides of the extended sleeve and a strip used to connect the sides of the package and form the top and bottom of the extended sleeve. As depicted in the drawings and described in the specification, this package is not easily manufactured using existing packaging equipment. In addition to the problems with the packaging, the patent also fails to disclose an effective and easy-to-use means of sealing the extended sleeve of this package between uses.

The opening must be sealed between uses to avoid moisture penetration of the package and, therefore, curing of the product within the package. The disclosed methods of sealing the opening include clamps, such as a tongue and groove scissor clamp; moisture-proof pressure-sensitive adhesive tape; a "ZIPLOC™" brand-type seal; and gaskets used in conjunction with spring-loaded compression, leverage clamping or screw action devices.

These methods have proven less than desirable in use. The more secure of the devices are difficult to use which increases the amount of time the package is open during use, thereby allowing moisture to enter and harden the material therein. Conversely, the sealing methods which are easy to use form seals of questionable integrity which allow moisture penetration into the package even when the seal is closed.

SUMMARY OF THE INVENTION

The present invention comprises an easy-to-use and extremely effective moisture-proof resealable closure incorporating mutually attracting magnetic strips to seal the opening of a package. The magnetic strips are mutually attracting over substantially their entire length to allow the package to be easily opened while also providing for essentially automatic resealing of the package after use.

The resealable closure of the present invention has many uses, but is especially useful for packages containing continuous length moisture-curable products such as orthopedic casting materials. Such products are particularly sensitive to ambient moisture which tends to penetrate through known sealing devices, causing waste of the product.

The magnetic closure system disclosed herein can be used to provide a package which can be opened to dispense product and resealed in a very short period of time, minimizing waste of the product due to exposure to ambient humidity.

In one preferred embodiment the present invention comprises opposing magnetic strips bonded to opposing opening sides of a package.

In another preferred embodiment the present invention comprises opposing magnetic strips backed by an additional layer, such as spring steel, and including clamps on both ends of the closure device to maintain its integrity. The spring steel provides additional rigidity to the magnetic strips which enhances the rapid closing action provided by the device. This particular embodiment can either be bonded to the opposing opening sides of a package or can be separate from the package so that it can be re-used with many different packages.

In another preferred embodiment, the present invention comprises an additional layer of stiffening materials bonded to the outside surfaces of the package before the magnetic strips are applied to the package. This embodiment is particularly useful for stiffer packaging materials which may have a tendency to pucker or wrinkle at the seal, thereby compromising seal integrity. The stiffening materials also assist the magnetic strips in sliding across the package during opening and closing and serve to hold the magnetic strips proximate the package by extending into end caps.

In another preferred embodiment, the stiffening material can be adhesively bonded to the package while, at the same time, being unattached to the magnetic closure assembly. This embodiment is particularly useful when the magnetic closure system is separated from the package for re-use on a number of packages and also allows wider opening of the package for better access to the contents therein.

Also contemplated within the present invention is a pouch for packaging continuous length moisture-curable orthopedic/casting products. The pouch preferably includes the magnetic closure system as disclosed above to provide a hermetic, moisture-proof resealable closure. The pouch can also include an opening which allows for easy and quick access to the product. The preferred designs minimize the length of the seal required to close the pouch while still providing adequate room for packaging a sufficient amount of the continuous length moisture-curable product.

Advantages of the pouch of the present invention include dramatically reduced foil packaging use and waste as opposed to those systems in which the entire length of the product must be encased in packaging material and reduced risk of pinholes leading to product failure due to moisture penetration of the pouch. The pinhole risk is decreased by minimizing creases and associated flex cracking in the laminated packaging material.

Another advantage is that the pouch design includes a gusset to provide an enlarged main storage area and a measure of self-collapsing action as product is dispensed which limits the entry of moisture during use. The pouch is also easily manufactured using existing packaging equipment.

The pouch of the present invention can also be placed in a rigid outer container along with compression means such as compressed elastomeric foam. In that embodiment the foam expands as the product is dispensed, thereby collapsing the pouch to minimize the entry of air and moisture during dispensing.

Also contemplated are inserts designed to be placed in an opening of the pouch, the inserts incorporating magnetic strips in hinged covers or removable lids.

In yet another embodiment, the invention comprises an easy-to-use and effective magnetically resealable moisture-proof pouch containing moisture-curable orthopedic splinting/casting product in bulk form. The pouch incorporates a frame disposed about an opening into the pouch which provides a mounting place for a moisture-proof magnetic seal.

Advantages of pouches manufactured according to the present invention include dramatically reduced foil packaging use and waste as opposed to those systems in which the entire length of the product must be encased in packaging material. The present invention also reduces risk of pinholes leading to product failure due to moisture penetration into the pouch. The pinhole risk is decreased by minimizing creases and associated flex cracking in the laminated packaging material which are inherent in many known package designs. The pinhole risk is also decreased simply by providing a pouch formed of a lesser amount of packaging material which can always possibly include pinholes formed during manufacturing.

Another advantage of the present invention is that the preferred pouch design includes a gusset to provide an enlarged storage area and a measure of self-collapsing action as product is dispensed which limits the entry of moisture during use. The pouch is also easily manufactured using existing packaging equipment.

The pouch according to the present invention also preferably includes retaining means for retaining the product proximate the opening of the pouch and spacing means for spacing the remainder of the product from the opening of the pouch. In the preferred embodiment, the retaining means and spacing means are combined into an insert placed in the pouch. The preferred retaining means comprises a slot spaced from the opening of the pouch with the product threaded through the slot to reach the opening of the pouch. The preferred insert also functions as the spacing means by preventing the product from sliding underneath the slot in the insert.

The present invention further comprises containers for pouches manufactured according to the present invention. The containers according to the present invention incorporate magnetic seal components used to reseal the pouches to provide a moisture-proof magnetic resealing system for dispensing the product stored in bulk form in the pouches.

The magnetically sealed pouches and associated containers according to the present invention can be opened to dispense product and resealed in a very short period of time as compared to known packaging systems for these materials, thereby minimizing waste of the product due to exposure to ambient humidity.

The magnetic components used to reseal the pouches are attached to access means such as hinged doors or removable covers which cooperate with the frames on the preferred pouches to accomplish hermetic resealing of the pouches.

The containers according to the present invention are preferably manufactured of substantially rigid materials and can either be reusable or disposable. Furthermore, the containers may include compression means such as compressed elastomeric foam. The compression means is used to collapse the pouch to minimize the entry of air and moisture when the pouch is open during dispensing.

These and various other advantages and features which characterize the present invention are pointed out with particularity in the claims annexed hereto and which form a part hereof. However, for a better understanding of the invention, and the advantages obtained by its use, reference should be made to the drawings which form a further part hereof, and to the accompanying descriptive matter, in which there are illustrated and described preferred embodiments of the invention.

BRIEF DESCRIPTION OF THE DRAWING

The invention will be further described with reference to the drawing wherein corresponding reference characters indicate corresponding parts throughout the several views of the drawing, and wherein:

FIG. 21 is a perspective view of one preferred pouch according to the present invention, incorporating a frame surrounding an opening in the pouch.

FIG. 22 is a perspective view of one embodiment of a combination according to the present invention, the combination including a container and the pouch of FIG. 21.

FIG. 24 is a perspective view of an alternative embodiment of a combination according to the present invention incorporating a structure forming one wall of a container and a door attached to the structure.

DETAILED DESCRIPTION OF THE PREFERRED EMBODIMENTS

Figure 1:
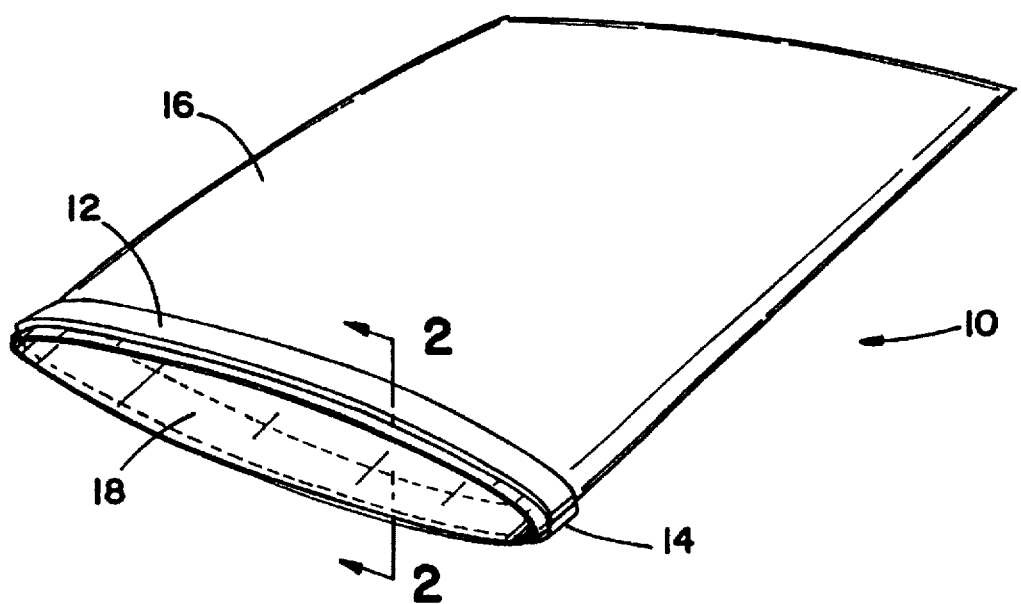
FIG. 1 is an end perspective view of a package for moisture-curable orthopedic splinting/casting materials, including one embodiment of the magnetic closure system of the present invention.

The pouches, closures and associated containers of the present invention have many uses, including food product packages, but are especially useful for packages containing continuous length moisture-curable products. Such products are particularly sensitive to ambient moisture which tends to penetrate through known sealing devices used to dispense the product in bulk form, causing premature curing and waste of the product.

A number of alternative preferred embodiments of the magnetic closure system according to the present invention are described below. In its simplest form, the magnetic closure system consists of two magnetic strips bonded to opposing sides of a package opening. The magnetic strips seal the package due to the mutual attraction between the opposing magnetic strips along substantially their entire lengths. The magnetic strips may both be magnets or one may be a magnet and the other may be a non-remanently magnetizable strip.

Magnetic strips useful in the invention include permanent magnet strips (referred to as "magnet strips") which are remanently magnetized with a relatively high remanent magnetization/saturation magnetization ratio and a high enough coercivity to prevent significant demagnetization, with magnetization (vector) components perpendicular to the long dimension of the strip, and/or magnetized with alternating polarity in adjacent sub-regions of the strip (e.g. zones or bands with dimensions small relative to the length of the strip).

Also included in the definition of magnetic strips for the purposes of the present invention are non-remanently magnetizable strips of ferromagnetic or ferrimagnetic material which are designated "non-remanently magnetizable" because their coercivity is too low to prevent substantial demagnetization when removed from the magnetizing fields of a magnetic strip.

Preferred closures of the invention utilize a first magnetic strip and a second magnetic strip, with a mutually attractive force acting between the first and second strips over substantially the entire length of the strips. Preferred closures of the invention further comprise first and second strips that have their respective first and second ends maintained in contact by a non-magnetic means (e.g. adhesives, mechanical clamping device, etc.). The first magnetic strip is preferably a remanently magnetized magnet strip. The second magnetic strip may either be a magnet strip with a remanent magnetization pattern adapted to provide mutually attractive forces with the first magnetic strip, or a magnetic strip of "non-remanently" magnetizable material which becomes magnetized by the external magnetic fields from the adjacent first magnetic strip, facilitating mutual attraction between the first and second magnetic strips.

In preferred embodiments of the invention, magnet strips comprise single domain particles of uniaxially anisotropic magnetic materials in a polymeric binder, oriented such that their preferred direction of magnetization is perpendicular to the surface of the magnet strip, as described in U.S. Pat. No. 2,999,275 (Blume), which is incorporated herein by reference. Preferred anisotropic magnetic materials include hexagonal-structured ferrites such as $BaFe_{12}O_{19}$, $SrFe_{12}O_{19}$, or $PbFe_{12}O_{19}$, and rare earth-transition metal materials such as $SmCo_5$ and neodymium-iron-boron compounds. These magnet strips are also preferably substantially flexible.

The preferred magnet strips are perpendicularly magnetized in alternating polarity bands extending along the long dimension of the strips, typically with 8 to 11 alternating polarity bands per inch of width across a 0.060" thick strip. Because the bands extend along the length of the magnet strip, the mutual forces of attraction between a first magnetic strip and a second magnetic strip are essentially uniform along the extent of the strips. In other selected embodiments, the alternating polarity bands may extend across the width of the magnet strip, providing some variation of the mutually attractive force along the length of the closure, but the variation is on a dimensional scale small enough that they are still mutually attracting over substantially the entire length of the closure.

Non-remanently magnetizable magnetic strips used in the present invention generally comprise thin metallic sheets of ferromagnetic materials such as iron, cobalt or nickel, or alloys containing these compounds. Other materials would include ferromagnetic or ferrimagnetic particles in a polymeric binder. Some of these materials may retain some of the magnetization induced by contact with a remanently magnetized magnet strip as preferred for the first magnetic strip (after the first strip is removed) but would not have sufficient "coercive force" to resist demagnetization by low level stray magnetic fields.

The preferred magnet strips of the invention are preferably combined with "non-remanently" magnetizable backing strips, adjacent the outer surface of the magnetic strip and opposite from the closure surface, to increase the magnetic field adjacent the closure surface and the resultant attractive forces. The preferred backing strips are discussed in more detail below.

An example of one preferred embodiment of the present invention is depicted in FIG. 1 where the package 10 includes a bag having opposing sides 16 and 18. An opening is formed in one end of the package 10 and opposing magnetic strips 12 and 14 are attached to the surfaces of the package 10 which allows for the package 10 to be easily and quickly sealed. The magnetic strips 12 and 14 may be inset from the opening of the package 10 to provide packaging material for grasping to open the package 10.

Figure 2:
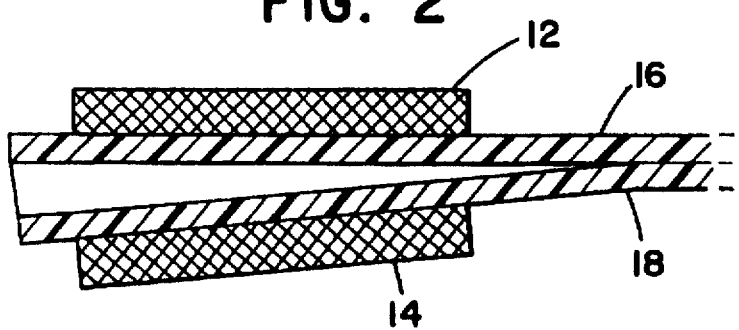
FIG. 2 is an enlarged cross-sectional view of the magnetic closure system depicted in FIG. 1.

A cross section of the seal depicted in FIG. 1 is shown in FIG. 2. Opposing magnetic strips 12 and 14 are bonded to the outside of the packaging layers 16 and 18. The magnetic strips 12 and 14 are preferably bonded along the entire length of the opening to reduce puckering or wrinkling of the packaging material caused by repeated opening and closing of the package 10, which otherwise might compromise the effectiveness of the seal. Preferred bonding methods can include pressure-sensitive adhesives, hot-melt adhesives, thermal bonding directly to the package with a heat seal layer or similar methods.

Although the magnetic strips are depicted as having a substantially rectangular profile, it will be understood that the magnetic strips could be provided with complementary, interlocking profiles to provide additional sealing ability.

Figure 3:
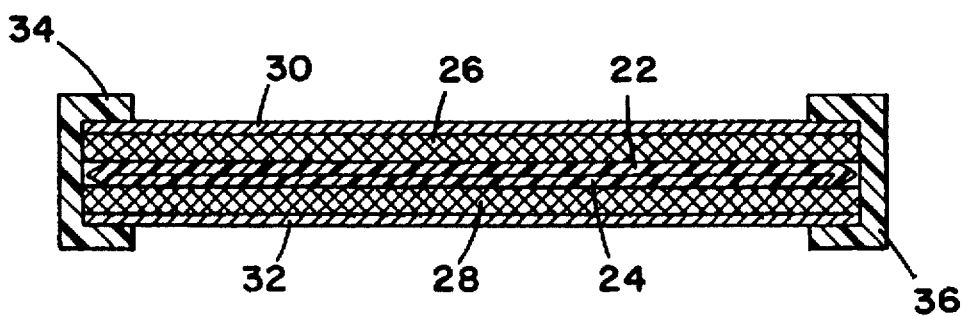
FIG. 3 is a cross-sectional view of another preferred embodiment of the magnetic closure system of the present invention.

An alternative embodiment of the magnetic closure system of the present invention is depicted in the cross-sectional view of FIG. 3. As shown there, the package has an opening including layers 22 and 24. The outside surface of each layer of packaging material is in contact with one of the two opposing magnetic strips 26 and 28.

Magnetic strip 26 includes a "non-remanently" magnetizable backing strip 30 along its side opposite from the packaging material while a "non-remanently" magnetizable backing strip 32 is disposed likewise on magnetic strip 28. Backing strips 30 and 32 are particularly useful if the packaging material 22 and 24 is relatively stiff as the backing strips act to increase the magnetic attractive force between magnetic strips 26 and 28 to aid in sealing of the opening.

Backing strips 30 and 32 are preferably constructed of a ferrous metal, most preferably spring steel. That type of material efficiently conducts the lines of magnetic flux on the sides of the magnetic strips opposite from the package, increasing the attractive force between the opposing magnetic strips 26 and 28. The backing strips 30 and 32 are preferably bonded directly to the back side of magnetic strips 26 and 28.

If no enhancement of the magnetic attraction is necessary, it will be understood that many other materials could be used to provide additional rigidity to the magnetic closure system such as wire, plastics, etc. with the primary consideration being that the backing strips should have an elastic limit great enough to avoid permanent deformation when the magnetic closure system is opened and closed repeatedly.

The preferred spring steel backing strips 30 and 32 are flat in cross-section, although spring steel backing strips having other cross-sectional shapes can be used to provide even greater rigidity to the magnetic closure system 20. Examples of other possible cross-sectional shapes include corrugated or grooved profiles, as well as any other shape which could impart a selected degree of rigidity to the magnetic closure system 20.

Also depicted in FIG. 3 are end caps 34 and 36 which are used to maintain the structural integrity of the magnetic closure system 20. End caps 34 and 36 do that by capturing the ends of the magnetic strips 26 and 28 and the spring steel backing strips 30 and 32. The preferred end caps are constructed of molded plastic. Alternate means of retaining the ends of the magnetic closure system together could include adhesives, screws, rivets, clamps or other devices.

The magnetic closure system depicted in FIG. 3 can be provided in two configurations. In the first, magnetic strips 26 and 28 are bonded to the packaging material 22 and 24 along their length. Such bonding is useful to reduce puckering or wrinkling of the packaging material at the seal, which could result in leaks through the seal. In the second, the magnetic strips 26 and 28 are not bonded to the packaging material. When the magnetic strips 26 and 28 are not bonded to the package, the closure system 20 can be easily transferred to a different package as needed.

Figure 4:
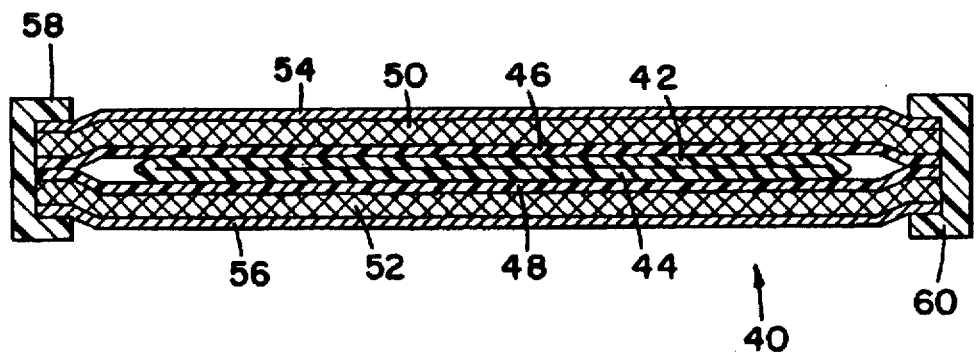
FIG. 4 is a cross-sectional view of another preferred embodiment of the magnetic closure system of the present invention.

FIG. 4 depicts another embodiment of the magnetic closure system 40 of the present invention. In this embodiment, each layer of packaging material 42 and 44 is bonded to a layer of stiffening material 46 and 48. The stiffening material 46 and 48 prevents the layers of packaging material from puckering or wrinkling during opening and closing, which otherwise might compromise the effectiveness of the seal. The preferred stiffening material 46 and 48 is a 4.0 mil (0.1 mm) plastic polyester film such as that used for transparencies used on overhead projectors, although many other materials such as polypropylene, polyethylene, nylon, polyacrylate, polystyrene, copolymers, polymer blends and polymer laminates, among others, could be substituted. The stiffening material 46 and 48 should also be as thin as possible to limit the effect the additional material has on the strength of the magnetic attraction between magnetic strips 50 and 52.

Surrounding the layers 46 and 48 of plastic film used as a stiffening material 46 and 48 are two magnetic strips 50 and 52 with spring steel backing strips 54 and 56 as described with respect to the above embodiments. The ends of the magnetic closure system 40 are held together with end caps 58 and 60 similar to the embodiment depicted in FIG. 3. The ends caps 58 and 60 retain the ends of the stiffening material 46 and 48, magnetic strips 50 and 52, and spring steel backing strips 54 and 56. By containing the ends of the stiffening material 46 and 48 (which is attached to the pouch), the magnetic closure system 40 is retained in place at the pouch opening.

Figure 5:
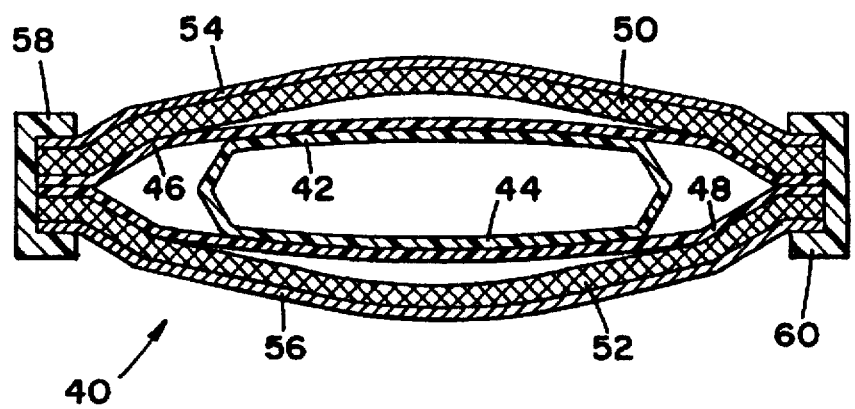
FIG. 5 is an end view of the magnetic closure system of FIG. 4 with the magnetic closure system in an open position.

The package opening including the magnetic closure system 40 of FIG. 4 is depicted in the open position in FIG. 5. As shown there, packaging layers 42 and 44 are separated to allow access to the interior of the package. Bonded to the packaging material are stiffeners 46 and 48 which assist in causing the closure system to automatically and positively close the package opening after the package contents adjacent the opening no longer obstruct the opening.

Magnetic strips 50 and 52 and backing strips 54 and 56 on both sides of the package are shown as pulled away from the opening of the package. This is the preferred embodiment, i.e., the magnetic strips 50 and 52 are not bonded to the stiffening material 46 and 48 except at the ends of the magnetic closure system 40. As a result, the magnetic strips/spring steel backing strips 50, 52, 54 and 56 can flex to a greater extent and/or slide over the stiffening material 46 and 48 as the package is opened and closed to aid in maintaining a wrinkle-free package opening.

Furthermore, if the end caps 58 and 60 are removable, the closure system comprising magnetic strips 50 and 52 and backing strips 54 and 56 can be transferred to another package to which stiffening materials 46 and 48 are already attached.

Figure 6:
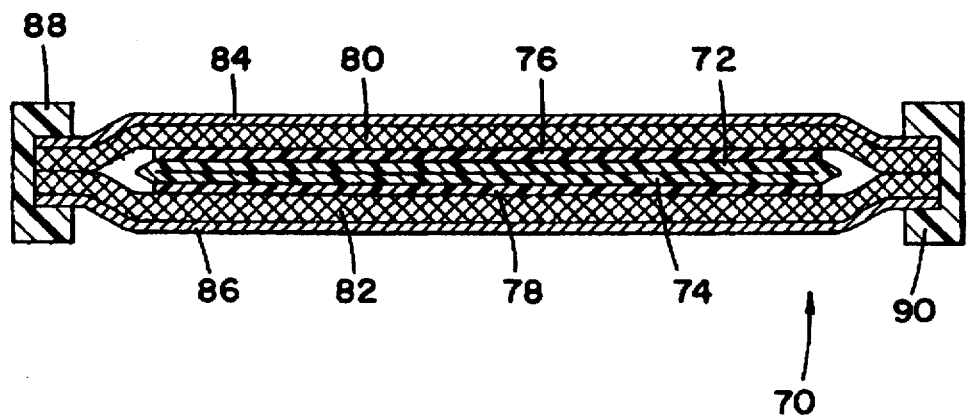
FIG. 6 is a cross-sectional view of another embodiment of the magnetic closure system of the present invention.

FIG. 6 discloses another embodiment of the magnetic closure system 70 of the present invention in which the layers of packaging material 72 and 74 have a stiffener material 76 and 78 bonded to them. Disposed about the stiffening materials 76 and 78 are two layers of magnetic materials 80 and 82 and spring steel backing strips 84 and 86. The magnetic strips 80 and 82 and spring steel backing strips 84 and 86 are bonded on both ends by end caps 88 and 90.

In this embodiment, the stiffening materials 76 and 78 are not bonded to the magnetic closure system 70. As a result, the magnetic closure system 70 comprising the magnetic strips 80 and 82, backing strips 84 and 86, and end caps 88 and 90 can be used to close the packaging material. When the package is ready to be discarded, the magnetic closure system 70 can be transferred to another package. In this way the benefit of the stiffening material 76 and 78 in maintaining the packaging material 72 and 74 in a wrinkle-free condition is retained while the magnetic closure system 70 can be re-used.

In addition to the flat embodiments of stiffening materials described above, stiffening materials with grooves or other features which ensure proper positioning of the magnetic closure systems on the packages are also contemplated.

One example of the easy opening feature of the magnetic closure system of the present invention was demonstrated by comparing the time required to open a "GLAD-LOCK™" brand sandwich bag using an interlocking type seal as opposed to the same bag with the interlock seal removed and fitted, instead, with a pair of magnetic strips similar to that depicted in FIGS. 1 and 2. The magnetic strips were "SCOTCH™ B1033" brand Magnet Tape (0.060" thick by 0.25" wide; Minnesota Mining and Manufacturing Company) adhered to the bag using "3M" brand Labelling Adhesive (No. 64-4612-4930-2), available from Minnesota Mining and Manufacturing Company, St. Paul, Minn. That magnet tape is now available under the trade designation "MGO™ B1033" brand magnet tape from Arnold Engineering, Inc., Norfolk, Nebr. The magnetic strips were offset from the end of the bag to allow material for grasping, similar to the standard design of the bags incorporating the interlocking seal.

To evaluate the ease of use, a group of people were timed while opening each bag, placing an object in the bag and resealing the bag. The mean time to complete the above operations using the standard "GLAD-LOCK™" brand bag was 7.9 seconds while the mean time using the modified bag was only 4.4 seconds—thereby indicating the relative ease with which bags incorporating the magnetic closure system of the present invention can be opened and closed.

Another example demonstrating the effectiveness of the magnetic closure system involved a standard commercially available pouch containing 3" "SCOTCHCAST PLUS™" brand moisture-curable orthopedic casting product, available from Minnesota Mining and Manufacturing Company, St. Paul, Minn. The packaging material used in the pouch is an aluminum foil-plastic composite, with the inner layer of plastic being "SURLYN™" ionomer resin available from E. I. DuPont de Nemours & Co., Wilmington, Del. One end of the pouch was fitted with a magnetic seal similar to that depicted in FIG. 3. The magnetic strip was "SCOTCH™ 1317" brand Magnet Tape (1" wide by 0.060" thick; Minnesota Mining and Manufacturing Company, St. Paul, Minn.), and was backed by flat spring steel strips (1" wide by 0.012" thick). That magnet tape is now available under the trade designation "MGO™ 1317" brand Magnet Tape from Arnold Engineering, Inc., Norfolk, Nebr. The ends of the magnetic strips and spring steel backing strips were clamped together. The magnetic strips were also adhesively bonded to the outside of the pouch material.

After modification, the magnetically sealed pouch, a control pouch with all sides heat sealed, and a pouch sealed with a tongue and groove scissor clamp on one end were all placed in an oven at 120° F. for accelerated aging. The samples were periodically checked for evidence of premature hardening. After twenty-six days in the oven the casting material in both the magnetically sealed pouch and the heat sealed control pouch was still soft—indicating that the magnetic seal had prevented moisture penetration into the pouch as well as a heat seal. In contrast, the product in the pouch sealed with a tongue and groove scissor clamp showed hardening after eighteen days.

Figure 7:
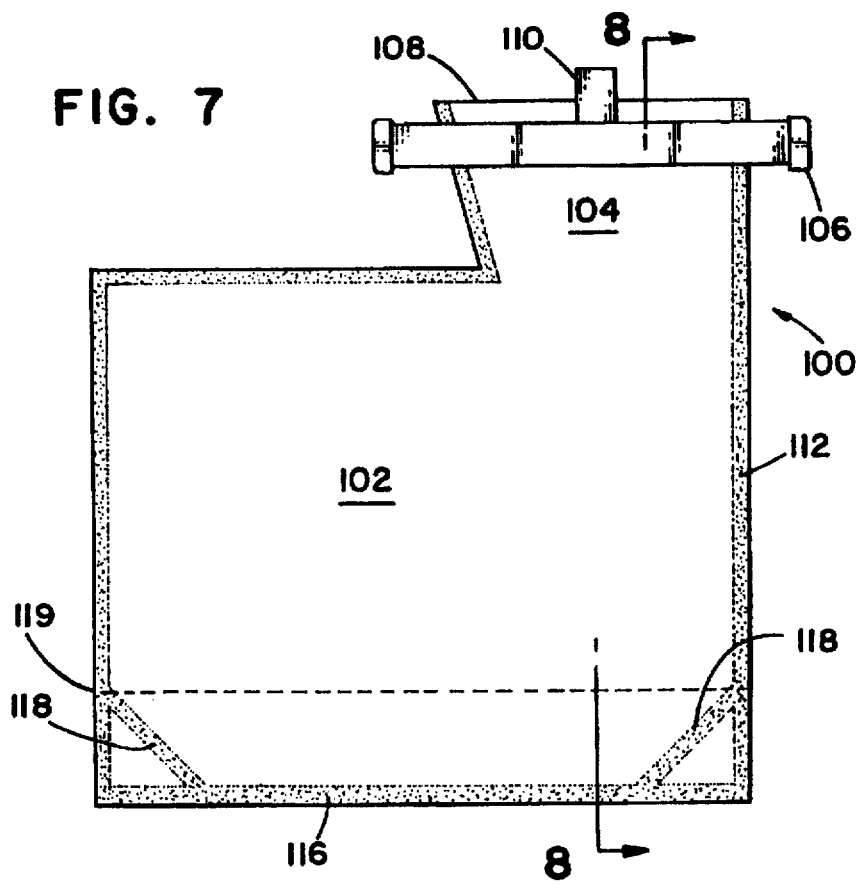
FIG. 7 is a plan view of a pouch for moisture-curable orthopedic splinting/casting material according to the present invention.

FIG. 7 depicts a pouch 100 constructed according to the present invention. This pouch 100 is especially useful for storing continuous length products, in particular, moisture-curable splinting/casting materials (e.g., containing isocyanate-functional resin). The preferred pouch 100 incorporates the magnetic closure systems described above to seal any openings made in the pouch 100 to dispense material contained therein.

The pouch 100 includes a main section 102 which is adapted to store a volume of the continuous length material and a sleeve 104 which extends off of the main storage area 102. Edge 108 of the pouch is preferably opened to gain access to the product stored in the pouch, and the magnetic closure system 106 is used to reseal the opening after use.

In the preferred embodiment the opening 108 includes tabs 110 to allow for easier and faster opening of the container. Other features to simplify opening of pouch 100 could be used in the place of tabs 110 such as ridges in the packaging material, finger holes in the packaging material, etc.

In its simplest form, the present invention can be manufactured using one piece of packaging material folded over and heat sealed along the edges or two pieces of packaging material heat-sealed together along their outside edges. The packaging material should be moisture-impervious to provide a pouch 100 that can be hermetically sealed to be moisture-impervious.

The preferred packaging material is a laminate with an outer layer of polypropylene over a layer of polyethylene over a layer of aluminum foil. The innermost layer is preferably SURLYN™ ionomer resin available from E.I. DuPont de Nemours & Company, Wilmington, Del., or a form of polyethylene to provide sufficient heat sealing properties.

Figure 8:
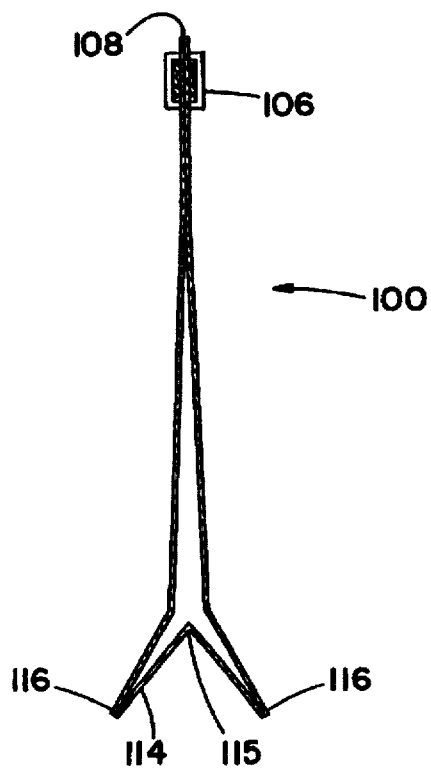
FIG. 8 is a cross-sectional view taken along line 8—8 in FIG. 7 depicting the gusseted bottom of one embodiment of the pouch of the present invention.

In the preferred embodiment as depicted in FIGS. 7 and 8 the bottom of the enlarged section 102 of the pouch is gusseted to provide additional volume in the pouch. The bottom gusset 114 includes the only crease 115 in the design. Crease 115 is not flexed repeatedly which significantly reduces the chances of pinholes forming along the crease 115.

To form the gusset, section 114 is heat sealed to the bottom edges 116 of the sides of the pouch 100. Four "corner" heat seals 118 are formed, each at an angle along a respective corner of the gusseted side of the pouch 100. The corner heat seals 118 are formed between the gusset section 114 and the sides of the main section 102, but not between the opposing faces (FIG. 8) of the gusset section 114. Heat seals 118 provide additional sealing at point 119 along the side of the pouch 100. It is at point 119 where the packaging material from both sides of the pouch and the gusset material 114 meet, which makes that point most vulnerable to leaks.

It is also contemplated that a pouch 100 could also be formed of a single piece of packaging material which is folded in a serpentine manner to form the gusset section 114, with the outside edges and folds heat sealed to maintain the shape of the pouch 100.

Figure 20:
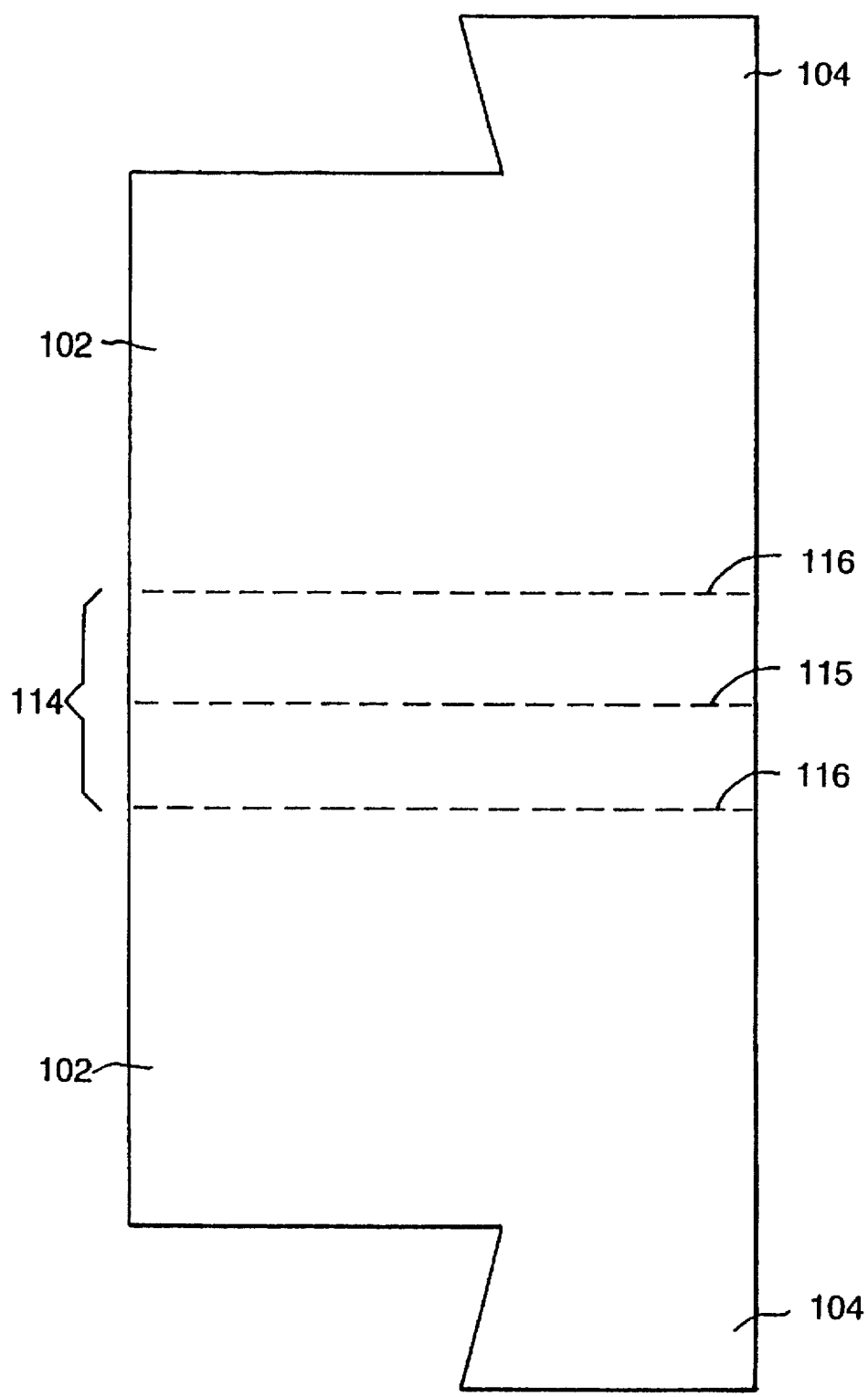
FIG. 20 is a plan view of a sheet of material cut to form the pouch of FIGS. 7 and 8.

As illustrated in FIG. 20, a single sheet of packaging material is cut to form mirror images of the major surfaces of the sleeve 104 and main portion 102 of the pouch 100, and the cut material is folded back upon itself to form the gusset section 114 and such that the corresponding edges of the major surfaces of the sleeve 104 and main section 102 are aligned. The aligned edges of the sleeve 104 and the main section 102, along with the aligned edges and bottom edges 116 of the gusset section 114, are then heat sealed to form the pouch 100. The open edge 108 is not heat sealed to allow removal of the splinting/casting material from the pouch 100. The bottom edges 116 are preferably heat sealed, even in the single sheet embodiment in which the bottom edges 115 are formed by folding the material back on itself.

Of course, the single sheet could be processed in a number of different ways and order of steps in accordance with this invention. For example, a web of the material could be folded to form the gusset, filled with the product, and sealed and cut as part of an automated form-fill-seal packaging process. In this example, the sheet illustrated in FIG. 20 would merely illustrate the outline of the finished pouch if the heat seals were deleted and the pouch unfolded.

Alternatively, a web of the material could be folded to form the gusset, and sealed and cut to form an open bag. As part of a second process the splinting/casting product would be placed in the open bag, and specially configured, but otherwise conventional heat sealing/cutting bars (not shown) could be used to heat seal and cut the pouch 100 to form the sleeve 104. A variation of this alternative bag-forming process could be employed in producing the pouches 150 and 160 of FIGS. 12 and 13, in which the channel-forming or guiding heat seals 156, 166 and 168 of those pouches are formed in the initial bag-forming process, and the open bag would be filled with the product and heat sealed along its remaining open edge.

It will be understood that numerous other alternative processes could be employed to manufacture the pouch of the invention.

Most preferably, as illustrated in FIGS. 7 and 8, the sheet of packaging material is folded to form a single gusset section 114, with a single gusset, although additional gussets (not shown) could be formed. For example, a second gusset section (not shown) could be provided along the opposite edge of the main section 102 from the gusset section 114.

It will be observed that the sleeve 104 is an integral extension of the main section 102 of the pouch 100.

Figure 14:
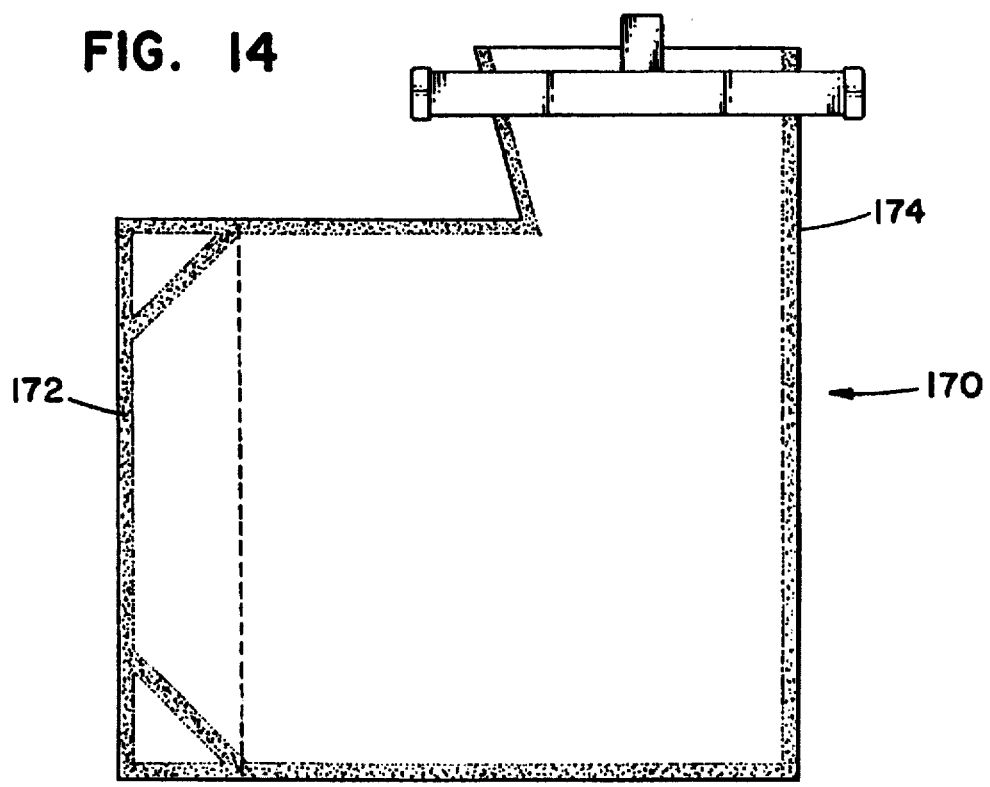
FIG. 14 is a plan view of an alternate pouch design according to the present invention.

An alternate embodiment is depicted in FIG. 14, where the gusset is located on a side 172 of the package 170 (adjacent the side containing the opening).

The gusseted pouches 100 and 170 described above both provide the advantage of being at least partially automatically collapsing as product is removed from them. That feature limits the amount of air entering the pouch as product is dispensed, thereby reducing the amount of moisture entering the pouch and prematurely curing the product contained therein.

The product may be placed in the pouch in any fashion which allows for easy removal. If, for example, the product is shaped like most moisture-curable orthopedic casting/ splinting products, it can be fan-folded or placed in the pouch in roll form. That particular configuration is depicted in FIG. 11, in which a roll of product is disposed in the main storage area 102 of pouch 100.

Figure 11:
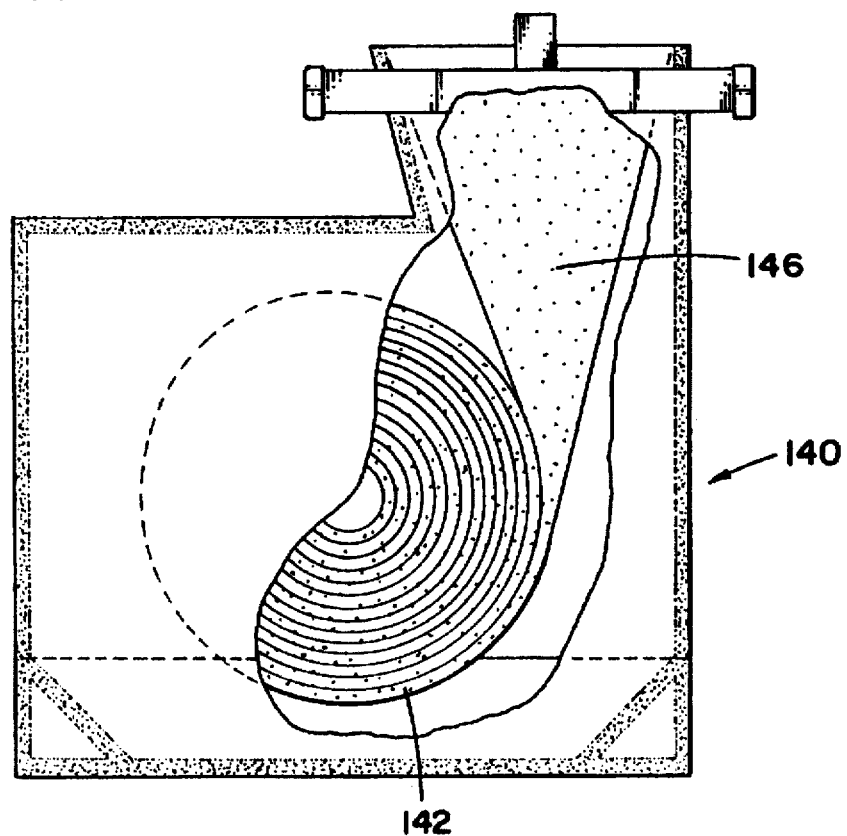
FIG. 11 is plan view of the embodiment depicted in FIG. 7, with the upper layer of packaging material partially cut-away to expose a roll of product contained therein.

In the embodiment depicted in FIG. 11, the product makes a 90-degree twist when passing from the enlarged storage area 102 through the extended sleeve 104. In spite of that twist, however, the product is still very easy to remove from the pouch. If desired, an insert could be placed in the pouch 100 to facilitate twisting of the product for easier dispensing.

A feature of the pouch which facilitates product removal is the widening of the opening 108 from the base of the sleeve 104. As shown best in FIG. 7, edge 108 is longer than the base of sleeve 104 (where it attaches to the main section 102 of the pouch). The edge 108 is preferably 25 to 100% wider than the width of the sleeve 104 at its base. The preferred range is approximately 33–50% wider.

Also in the preferred embodiment, the base of sleeve 104 is approximately the same width as any product stored in the main section 102. That ensures a snug fit around the product as it leaves the main section 102 of the pouch 100 which limits the amount of air entering the pouch 100 when opening 108 is used to dispense the product. Limiting that width also reduces the possibility of the product falling back into the main section 102 of the pouch 100.

Figure 9:
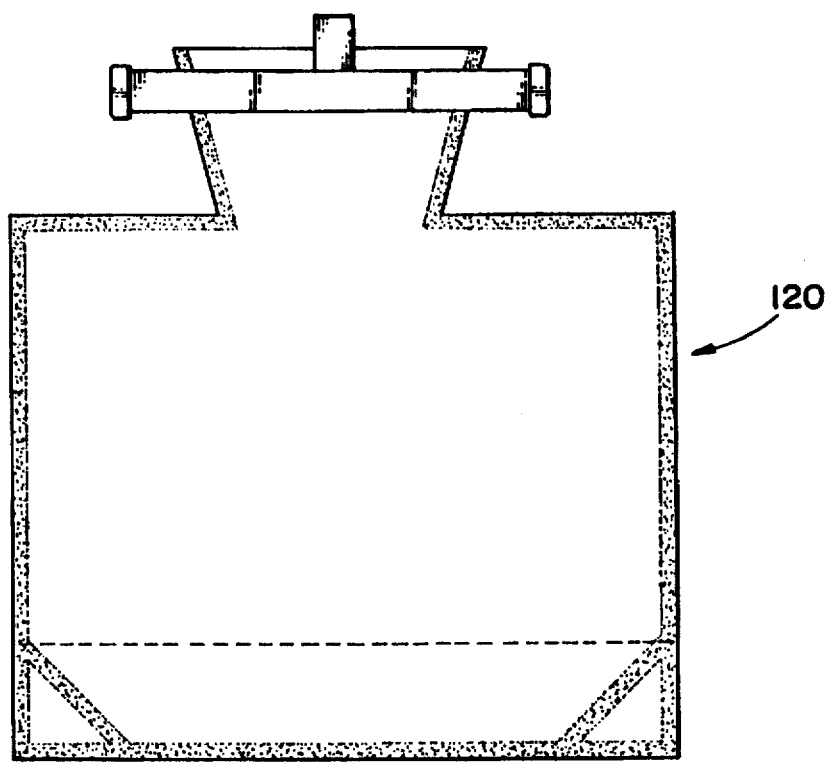
FIG. 9 is a plan view of an alternate pouch design according to the present invention.

As illustrated in FIG. 9, the sleeve can be at the center of the pouch as well as at the side as illustrated in FIG. 7.

In the preferred embodiment, the pouch is used while lying in the flat or horizontal position with a continuous length of product laying on its side enclosed within the pouch. This orientation facilitates dispensing of the product and is particularly important in the case of resin-coated sheets used as the curable reinforcing material. The resin content should also be low enough that significant resin migration, i.e., pooling does not occur. This is especially true if the resin is of relatively low viscosity. Alternatively, the product could be dispensed with the pouch and product in a vertical or upright position.

Means other than limiting the width of the opening as described above may also be provided to prevent the casting tape/splinting product from falling back into the enlarged storage area 102 during use, transport or storage. Examples of such means could include a textured surface on the inside surfaces of sleeve 104 which would make it easy to pull the product out of the pouch 100, but difficult for the product to return back into the pouch. Examples of such surfaces could include a fish scale-type texture or fabric with a directional nap which presents little or no drag in one direction and significant drag in the opposing direction.

The gusseted pouch of the present invention can be closed by any number of means including the magnetic closure systems described above, as well as other known closures, e.g., interlocking strips, pressure sensitive adhesives, malleable metal strips, scissor clamps and others.

Figure 10:
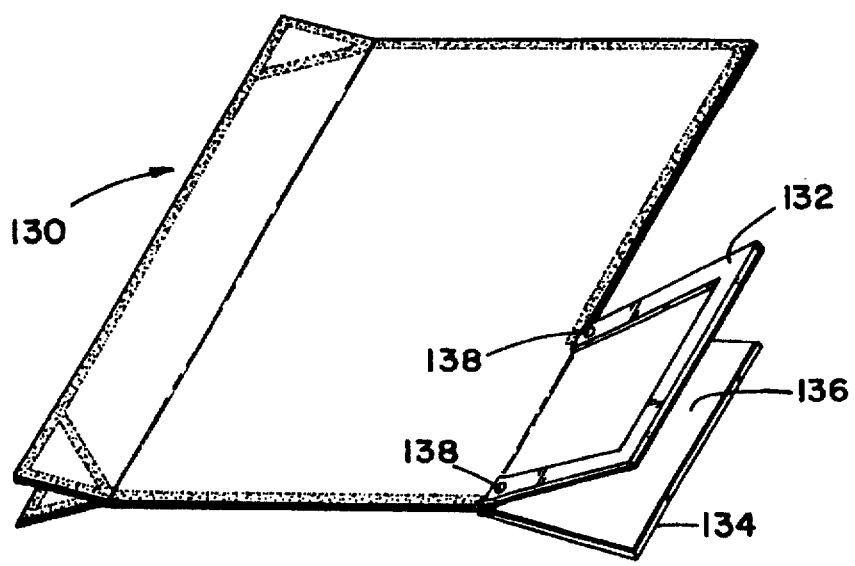
FIG. 10 is a perspective view of an alternate pouch design according to the present invention.

The preferred devices for closing the opening 108 of the pouch 100 are the magnetic closure systems disclosed above. In addition to the substantially linear magnetic closure systems described above, an alternate magnetic closure system, depicted in FIG. 10, could include a substantially U-shaped pair of opposing magnetic strips 132 and 134 located on the extension section of the preferred pouch 130.

The U-shaped closure system would be designed substantially similarly to the linear magnetic closure systems and would provide better access to the product contained in the pouch 130. An advantage of this closure system over the substantially linear magnetic closure systems is that there is no need to push the product back into the sleeve after cutting to ensure adequate sealing, as the cut in the product could be made within the U-shaped area and the upper flap of the sealing area could drop down onto the lower flap, thereby forming a substantially hermetic seal. The magnetic strips 132 and 134 may be placed on the outside (as shown) or may be bonded to the inner sides of the pouch 130 to ensure that a hermetic, moisture-proof seal is attained. This can be accomplished using hot-melt adhesives, pressure-sensitive adhesives, combinations thereof or their equivalents.

Figure 12:
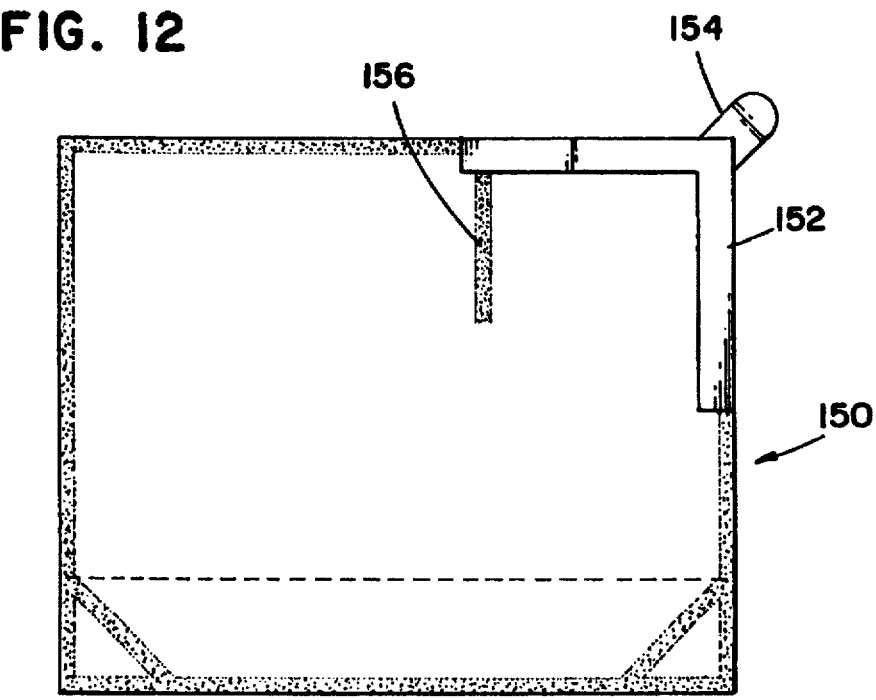
FIG. 12 is a plan view of an alternate pouch design according to the present invention.
Figure 13:
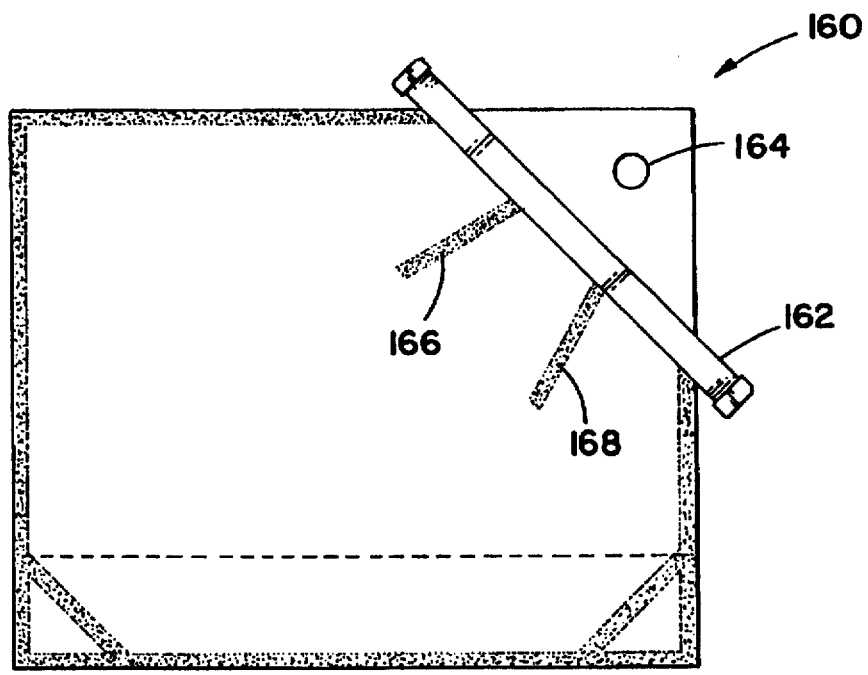
FIG. 13 is a plan view of an alternate pouch design according to the present invention.

Alternate preferred embodiments of the pouch of the present invention are depicted in FIGS. 12 and 13. In FIG. 12, the pouch 150 is constructed without a sleeve as depicted in FIG. 7. Instead, the opening is located on a corner of the pouch 150. Magnetic strip 152, comprising perpendicularly intersecting sections, is attached to the upper side and an opposing magnetic strip (not shown) is attached to the opposing side of the pouch 150. Tab 154 is added to aid in opening the pouch 150 to dispense the product inside.

The pouch 160 in FIG. 13 is also constructed without a sleeve. In this embodiment, the magnetic closure system 162 is placed diagonally across a corner of the pouch 160. In this particular embodiment, an optional finger hole 164 is provided in the packaging material extending beyond the magnetic closure 162 to aid in opening the pouch 160.

In the design of FIGS. 12 and 13, it may be desirable to heat seal the pouch material together within the storage portion to guide the material in the pouch 150 or 160 towards the opening. In FIG. 12, additional heat seal 156 is depicted which extends into the pouch 150. Such an additional heat seal 156 may also help prevent product in the pouch 150 from falling back away from the opening.

FIG. 13 depicts the use of two additional heat seals 166 and 168 which extend into the pouch 160, thereby forming a channel into the pouch 160 which can be used to guide material in the pouch 160 towards the opening and help prevent product in the pouch 160 from falling back away from the opening.

Figure 15A:
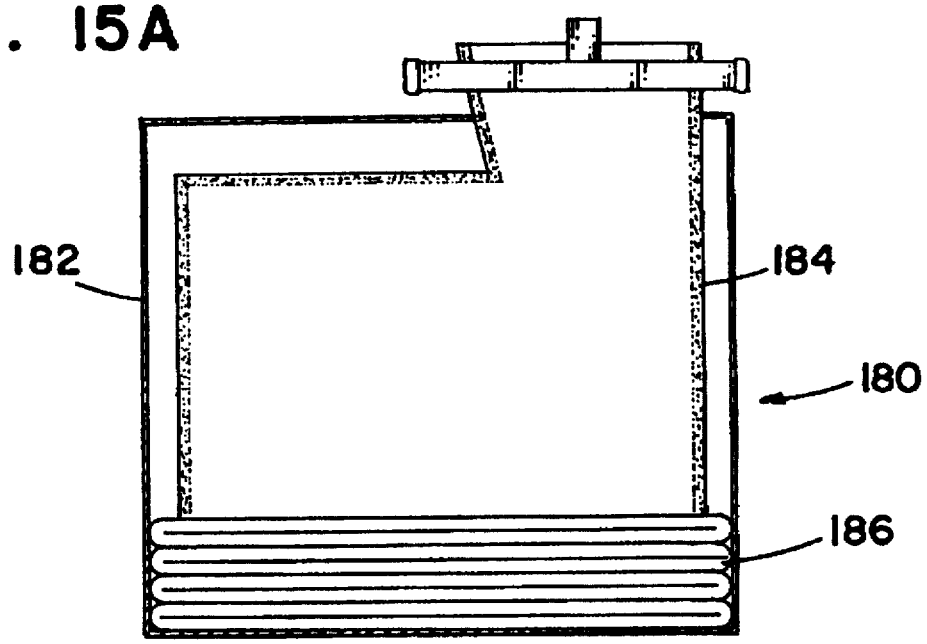
FIG. 15A is a partially cut-away side view of a pouch of the present invention located in a box with compressed foam, wherein the side panel of the box is removed to show the contents therein.
Figure 15B:
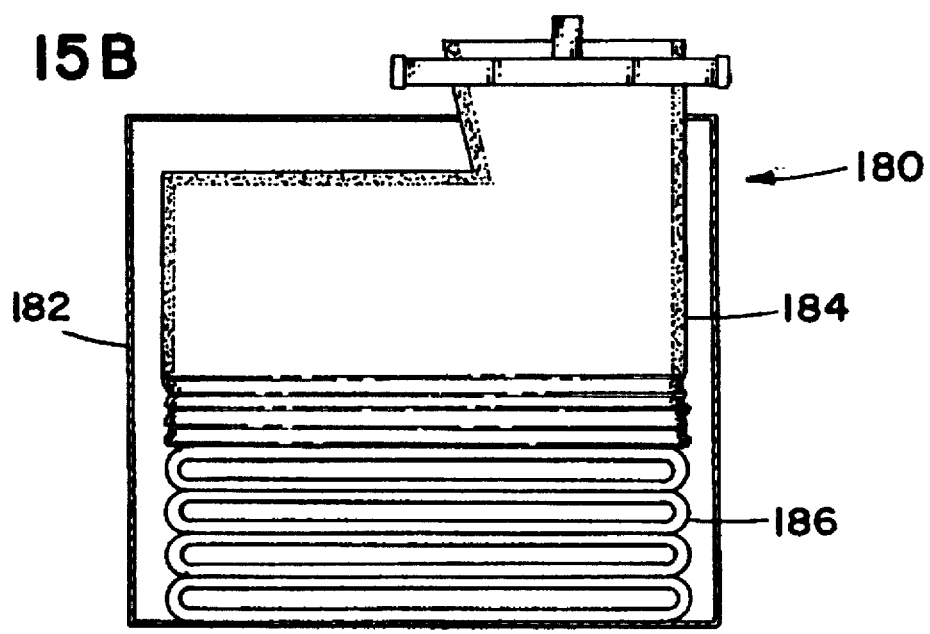
FIG. 15B is similar to FIG. 15A, with the foam shown as expanded due to the removal of product from the pouch.

FIGS. 15A and 15B depict yet another preferred embodiment of the present invention. In this embodiment the pouch 184 (containing product) is provided inside of a box 182. Also located in the box 182 are layers of compressed elastomeric foam 186. Also contemplated is the use of a single piece of elastomeric foam in place of layered foam 186. Although the foam 186 is depicted as being outside of pouch 184, it will be understood that it can also be placed within pouch 184 to provide many of the same benefits.

As depicted in FIG. 15A, the foam 186 is fully compressed before any product is dispensed from the pouch 184. Turning to FIG. 15B, as product is dispensed, the foam 186 expands to compress the pouch 184. That concurrent expansion of the foam 186 and compression of the pouch 184 limits the amount of air entering the pouch 184 as product is dispensed, thereby reducing the amount of moisture entering the pouch 184 which also reduces premature curing of the product contained therein.

All of the pouch designs discussed above are preferably placed in an outer protective covering or box. Boxes made from printed cardboard or printed corrugated cardboard are most preferred.

It will be understood that other means of compressing the pouch could be used in the place of compressed foam. Such means could include springs, pressurized bladders or other devices.

It will also be understood that a rigid container of any appropriate shape could be used in place of the box 182 depicted in FIG. 15. In addition, this concept could be adapted for use with any of the alternate preferred embodiments of the pouch as discussed above.

FIGS. 16–19 depict two embodiments of alternate closures incorporating the magnetic strips as discussed above. Like those closures, the closures depicted in FIGS. 16–19 also provide a substantially moisture-proof seal that is easy to use and to close after use.

Figure 16:
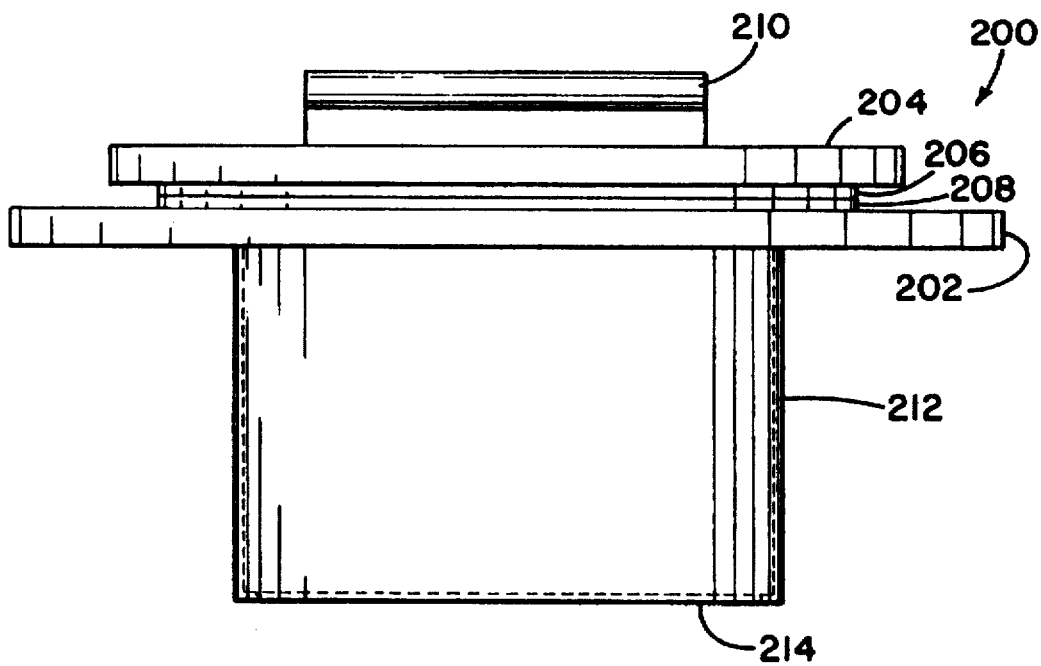
FIG. 16 is a side view of one embodiment of an insert designed to be placed in the pouch of the present invention, the insert incorporating magnetic strips for sealing.
Figure 17:
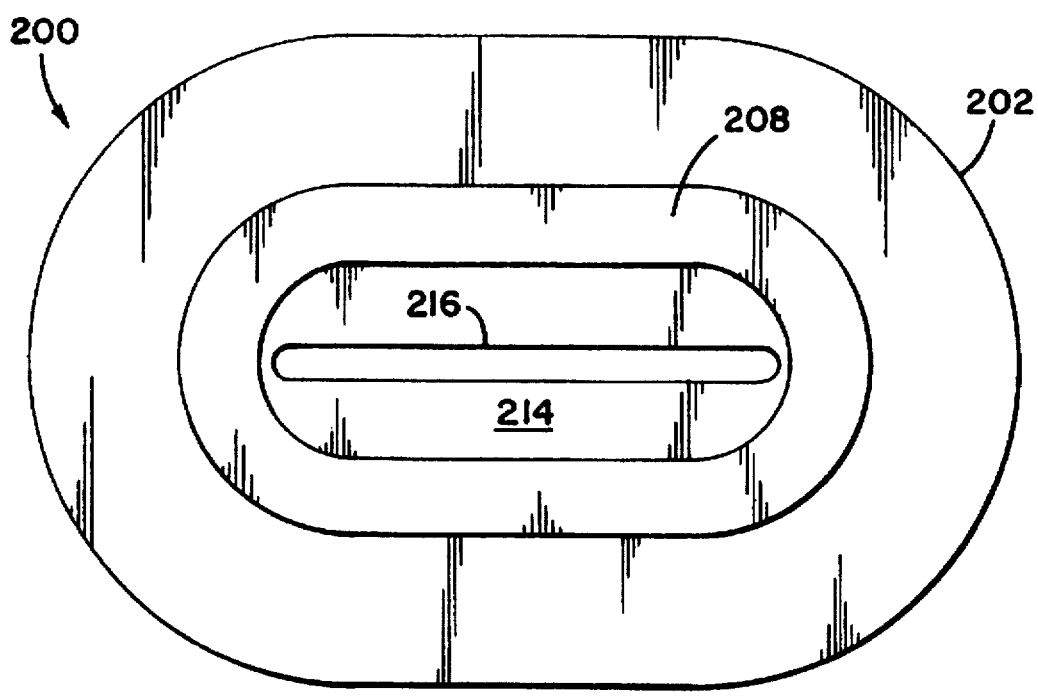
FIG. 17 is a top view of the insert of FIG. 16.

Referring to FIGS. 16 and 17, the magnetic closure 200 comprises a base plate 202. One magnetic strip 208 is bonded to the base plate 202. An opposing magnetic strip 206 is attached to lid 204, which is removed from the closure 200 as depicted in FIG. 17. Lid 204 preferably includes a handle 210 extending from its upper surface to facilitate handling of lid 204.

Closure 200 also preferably includes a lower extension 212 extending from the lower surface of the base plate 202. Lower extension 212 is cylindrical with an oval-shaped cross-section as depicted in FIG. 17. In one preferred embodiment the lower extension 212 includes a bottom surface 214 with a slot 216 formed in the bottom surface 214. In use with orthopedic casting splinting material (not shown), the material is threaded through slot 216 which helps to keep the material from falling into the pouch between use. To accomplish that, slot 216 is sized to approximate the cross-section of the material threaded through it. Alternatively, a diaphragm of neoprene or other stiff material can be placed around the slot 216 to hold the material between uses. In addition, the smaller opening (and diaphragm, if used) may reduce the amount of moisture entering the pouch when lid 204 is removed for the dispensing of material.

The pouch material (not shown) is preferably bonded to either the upper or lower surface of the base plate 202. The pouch material can be bonded to the base plate 202 through heat sealing, adhesives or any other method which provides an adequate hermetic, moisture-proof seal. In the preferred embodiment, the base plate 202 is manufactured from low density polyethylene which is conducive to heat sealing with the preferred pouch material. Portions of closure 200, including base plate 202 could also be manufactured of any other suitably moisture-impervious material, such as metals, plastics, etc. which could be bonded to the packaging material using any suitable means such as adhesives, mechanical fasteners, etc.

Figure 18:
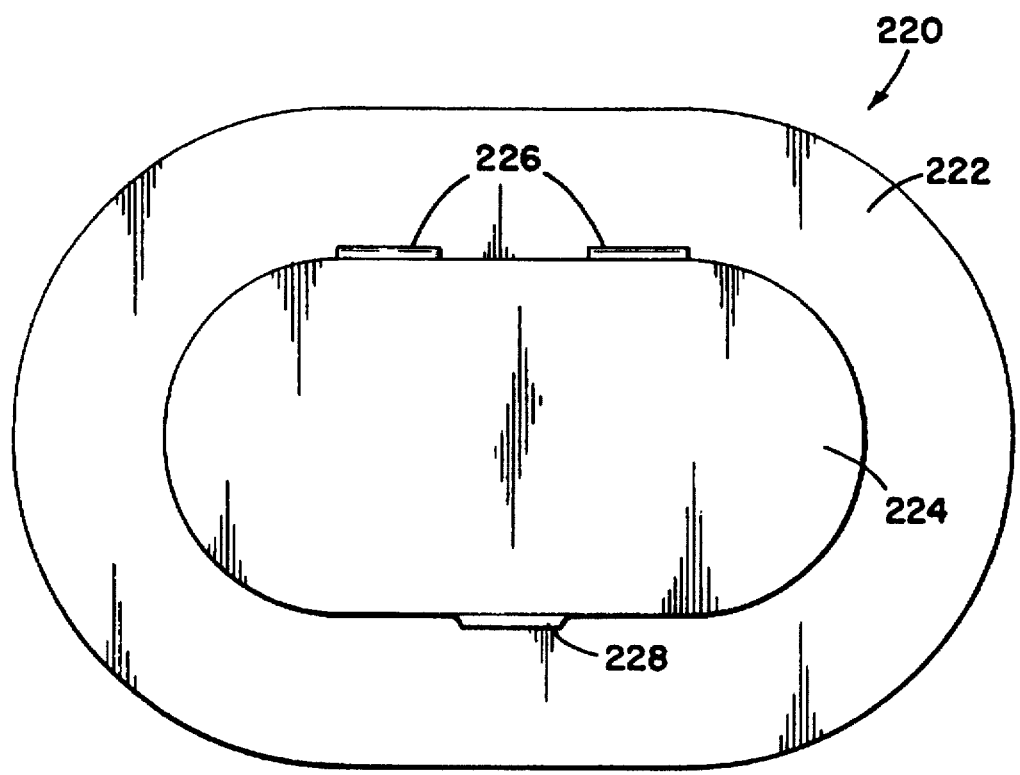
FIG. 18 is an alternate embodiment of an insert designed to be placed in the pouch of the present invention, the insert incorporating magnetic strips for sealing.
Figure 19:
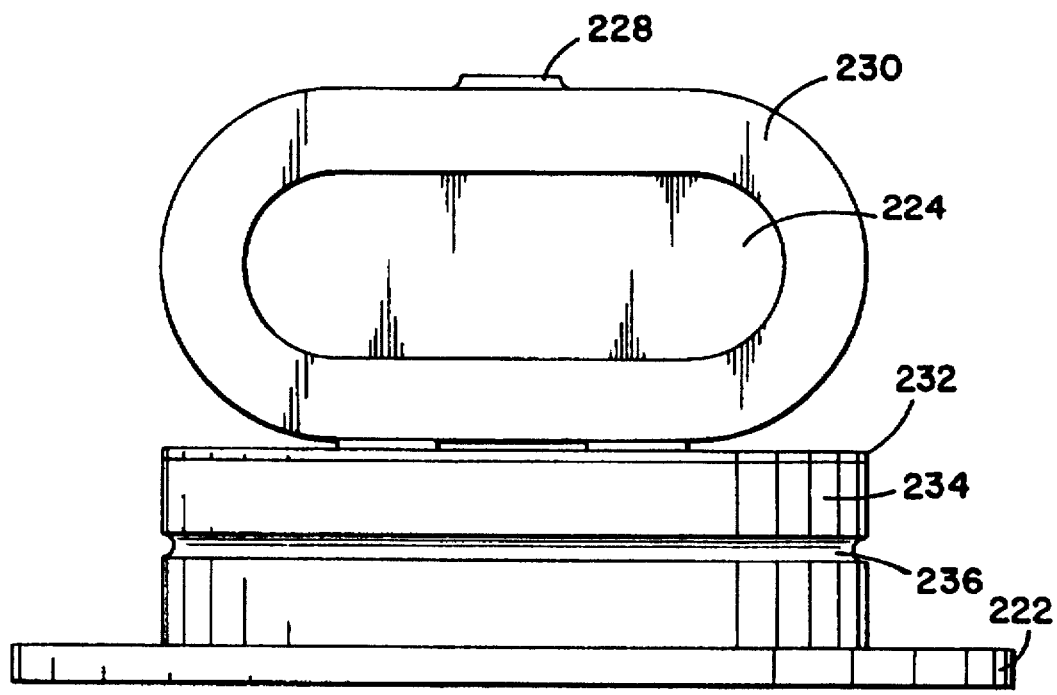
FIG. 19 is a side view of the insert of FIG. 18.

Referring now to FIGS. 18 and 19, where closure 220 is depicted. Closure 220 includes a base plate 222 above which upper extension 234 rises. Upper extension 234 is cylindrical and has a cross-section that is substantially oval-shaped, as best seen in FIG. 18. Upper extension 234 also includes groove 236 around its outer circumference. Groove 236 is useful for receiving the sidewall of a rigid container (not shown) to maintain the closure 220 in a stable position when the pouch (not shown) to which the closure 220 is attached is placed in a rigid container as depicted in FIGS. 15A and 15B.

Alternatively, if upper extension 234 and groove 236 protrude from a rigid container, a removable clip (not shown) could be placed around upper extension 234 and inserted into groove 236 to secure the closure in a stable position relative to the rigid container.

Magnetic strip 232 is attached to the upper surface of upper extension 234. An opposing magnetic strip 230 is attached to lid 224 to provide a substantially hermetic seal to closure 220. In the embodiment depicted in FIGS. 18 and 19, lid 224 is connected to upper extension 234 by a pair of hinges 226 and also includes tab 228 for opening lid 224.

The pouch material (not shown) is preferably bonded to either the upper or lower surface of the base plate 222. The pouch material can be bonded to the base plate 222 through heat sealing, adhesives or any other method which provides an adequate seal. In the preferred embodiment, the base plate 222 is manufactured from low density polyethylene, polypropylene or other materials which are conducive to heat sealing with the preferred pouch material. Portions of closure 220, including base plate 222 could also be manufactured of any other suitably moisture-impervious material, such as metals, plastics, etc. which could be bonded to the packaging material using any suitable means such as adhesives, mechanical fasteners, etc.

Like bottom surface 214 in closure 200, base plate 222 can also be constructed with a slot (not shown) to prevent orthopedic casting material (not shown) from falling into its container (not shown) between dispensing.

In either of the embodiments depicted in FIGS. 16 or 18, each of the magnetic strips 206, 208, 232, 230 are preferably formed out of a single sheet of the magnetic material used in the elongated strips of the magnetic closures as described above. It will be understood that the oval-shape of the closures 200 or 220 are preferred shapes and that any closed geometric figure that provides a substantially hermetic seal could be substituted for the oval shape of closures 200 and 220.

It will also be understood that the various features of each embodiment depicted in FIGS. 16–19 could be combined in a single closure. For example, the lid 204 of the closure 200 could be attached to base plate 202 with hinges or closure 220 could include a lower extension such as 212 in closure 200.

Additional Preferred Embodiments

FIGS. 21–26 depict yet additional preferred embodiments of pouches used to store moisture-curable orthopedic splinting/casting products and containers used to store the pouches for shipping and/or dispensing of the products in the pouches.

Referring to FIG. 21, a preferred embodiment of a pouch 240 constructed according to the present invention includes a gusset 242 and two sides 243 and 244. Pouch 240 is constructed similarly to pouches described in FIGS. 7–14 and 20, all of which can be manufactured using a single piece of moisture-impervious material which is heat sealed along the edges or a number of pieces of packaging material which are combined to form the gusseted pouch 240.

A primary difference between pouch 240 and those depicted in FIGS. 7–14 and 20 is the removal of the sleeve depicted in those pouches. As described above, the sleeves were provided for access to the main storage areas of the pouches. Pouch 240, however, incorporates an opening 246 in the gusset 242 of pouch 240 to provide access to the interior of the pouch 240.

Although depicted as being located in the gusset 242 of pouch 240, it will be understood that opening 246 could alternately be located on either side 243 or 244 of pouch 240. Location of the opening 246 in gusset 242 does, however, maximize space utilization of the product within the pouch 240. As described above, the product can be fan-folded (see FIGS. 15A & 15B) or rolled (see FIG. 11) within pouch 240.

In its simplest form, the opening 246 comprises a slit formed through the material of the gusset 242 which is within the void 249 in frame 248. Alternately, substantially all of the packaging material within the void 249 in frame 248 could be removed to provide a wider opening 246 in pouch 240.

If opening 246 does comprise a slit, it is preferably reinforced to prevent excessive ripping or tearing of the packaging material which could jeopardize the integrity of the pouch 240. Suitable reinforcements include tapes, films, etc., which are attached to the packaging material. The preferred reinforcement is a ¾" wide pressure-sensitive filament tape available from Minnesota Mining and Manufacturing Company, St. Paul, Minn., under the trade designation "SCOTCH™" filament tape No. 898.

The opening 246 can be formed during manufacturing and covered with a suitable moisture proof adhesive sealing tape 250 as depicted in FIG. 21. The preferred tape for that purpose is available under the trade designation "SCOTCH-PAK™" sealing tape, from Minnesota Mining and Manufacturing Company, St. Paul, Minn. As shown, the tape 250 can be sized to adhere to the frame 248 over void 249. In the alternative, tape 250 could be adhered to the packaging material lying within void 249 defined by frame 248.

In the alternative, the opening 246 can be formed using a tear strip (not shown) such as that used in packaging of food and other products requiring substantially hermetic packaging that can be easily opened by a customer. The details of constructing a package with a tear strip will be well known to those skilled in the art. It will be understood that opening 246 can also be made by the customer using a scissors or other instrument when product is desired to be removed from the pouch 240.

Surrounding opening 246 is a frame 248 which, in the preferred embodiment, is attached to the exterior of the pouch 240. Alternatively, the frame 248 could be attached to the interior of the pouch 240. Frame 248 defines a void 249 which exposes the area in the pouch 240 in which the opening 246 is formed (during manufacturing or by the user).

Frame 248 preferably provides a substantially planar and rigid surface for sealing of the opening 246. In the preferred embodiment frame 248 is constructed of a ferromagnetic or ferrimagnetic material which is subject to magnetic attraction when placed in the magnetic field of a remanently magnetized material. One material which could be used to form frame 248 include "PLASTIFORM™ B-1033" remanently magnetized composite material available from Arnold Engineering, Inc., Norfolk, Nebr. The preferred material used to form frame 248 is ferrous metal, preferably 1010 steel, although any non-remanently magnetizable or remanently magnetized material which can be formed with the required level of rigidity could be used to form frame 248.

It is important that the frame 248 provides a substantially planar, rigid surface to provide adequate sealing over the opening 246 as will be described below. The attachment of the packaging material of pouch 240 to frame 248 must be accomplished to ensure that the interface between the pouch 240 and frame 248 is substantially wrinkle-free to avoid leakage of air and moisture into the pouch 240 through that interface.

In the preferred embodiments, the frame 248 is attached to the pouch 240 using a hydrophobic adhesive with low moisture vapor permeability to prevent moisture penetration into the pouch 240 through the adhesive bond between the frame 248 and gusset material 242. Examples of hydrophobic adhesives which could be used to attach the frames 248 to pouch 240 could include, but are not limited to, adhesives based on natural rubber, butyl rubber, polyisobutylene, polyisoprene, and styrene-butadiene (commercially available under the trade designation "KRATON").

Many other means of attaching frame 248 to gusset 242 could also be used in place of hydrophobic adhesives, such as heat sealing (where the frame includes a heat sealable material on at least one surface) and any other means which provides a bond between the frame 248 and pouch 240 which is substantially moisture impervious.

Although depicted as including gusset 242, it will be understood that the gusset 242 is present in the preferred embodiments to maximize the volume of the pouch 240 for a given amount of packaging material. The gusset 242 also minimizes creasing of the sides 243 and 244 of pouch 240 which helps to prevent pinholes in the packaging material. Alternatively, pouches according to the present invention could be constructed without a gusset 242, in which case the opening 246 would be formed in one side 243 or 244 of the pouch 240. Additionally, it will be understood that pouch 240 could incorporate one or more additional gussets (not shown).

Other features contemplated for inclusion into the preferred pouch 240 include a leader attached to the moisture-curable orthopedic splinting/casting product to facilitate initial removal of the product after the pouch 240 is opened. In embodiments incorporating moisture proof adhesive sealing tape to seal the opening 246 or a tear strip system to form the opening 246, the leader could be attached to the tape or tear strip to further facilitate initial removal of the product from the pouch 240.

In addition, although only a single roll of orthopedic splinting/casting material is described above as a candidate for storage in pouches similar to 240, it will also be understood that a plurality of smaller rolls of water/moisture curable casting tapes, for example, isocyanate-functional resin coated sheet materials, could also be stored in pouches similar to pouch 240.

In such a design, a number of rolls of casting tape could be stored in pouch 240 for delivery to a customer. The customer would then place the pouch 240 into one of the containers described below to dispense individual rolls of the casting tape and avoid prematurely curing them after pouch 240 has been opened.

To further prevent premature curing, the rolls of casting tape can be packaged individually before being placed within the pouch 240. Individually packaging the rolls would allow a clinician to remove one or more rolls from the pouch 240 for use with a patient located a distance from the pouch 240, thereby avoiding the necessity of taking the entire pouch 240 to the patient to prevent premature curing of the casting tape.

Suitable materials for individual, or secondary, packaging of individual rolls of casting tape could include polyolefins, polyesters, metallized polyesters, polyamides, and multi-component laminates incorporating foils. The preferred material is a low density polyethylene commonly found in sandwich bags. It will be understood that the secondary packaging material need not necessarily be completely moisture-impervious but should at least slow the penetration of moisture into the individual packages to allow a clinician more working time before the product cures.

Referring now to FIG. 22 which depicts one preferred embodiment of further packaging pouches similar to pouch 240 described above. As shown there, pouch 240 is packaged within an outer container 260 which can be used for shipping pouch 240 as well as containing pouch 240 during dispensing of product from pouch 240. The preferred container 260 is formed of corrugated cardboard and is designed to be disposed with pouch 240 after the product is removed.

Container 260 preferably includes a hinged door 262 which opens to reveal frame 248 attached to pouch 240. Also in the preferred embodiment, the door 262 is precut into container 260 using perforations through the preferred material of container 260. To facilitate opening of door 262, a finger tab 265 is formed in the container 260. Although the preferred material is corrugated cardboard, it will be understood that other materials providing sufficient protection and rigidity for shipping and dispensing the product could be used for container 260.

Figure 27:
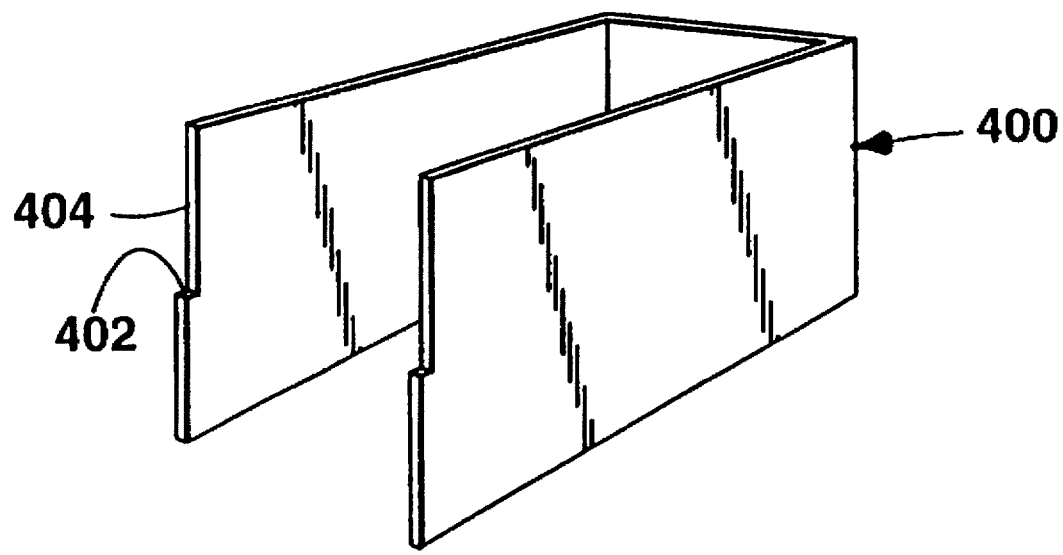
FIG. 27 is a view of an insert for use in the container of FIG. 24 to hold the pouch in position in the container.

In the preferred embodiment, frame 248 is secured proximate opening 263 for door 262 in container 260. Suitable means for securing the frame 248 proximate opening 263 in container 260 include adhesives, mechanical fasteners, etc. The preferred means are tabs extending laterally outwardly from the frame 248, and an insert 400 (FIG. 27) in the container 260. The insert 400 has opposite front edges each cut to form a shelf 402 and a tab-receiving space 404 for closely receiving the tabs of the frame 248 and holding the frame 248 against the front end of the container 260 in proper alignment with the door 262 and opening 263. The arrangement is such that the top of the container 260 may be opened and the tabs of the frame 248 of the pouch 240 slid down into the tab-receiving space 404 until the tabs engage the shelf 402. The top of the container 260 is then re-closed. As an alternative to the tabs, the opposite edges of the frame 248 may be received in the spaces 404.

Figure 28:
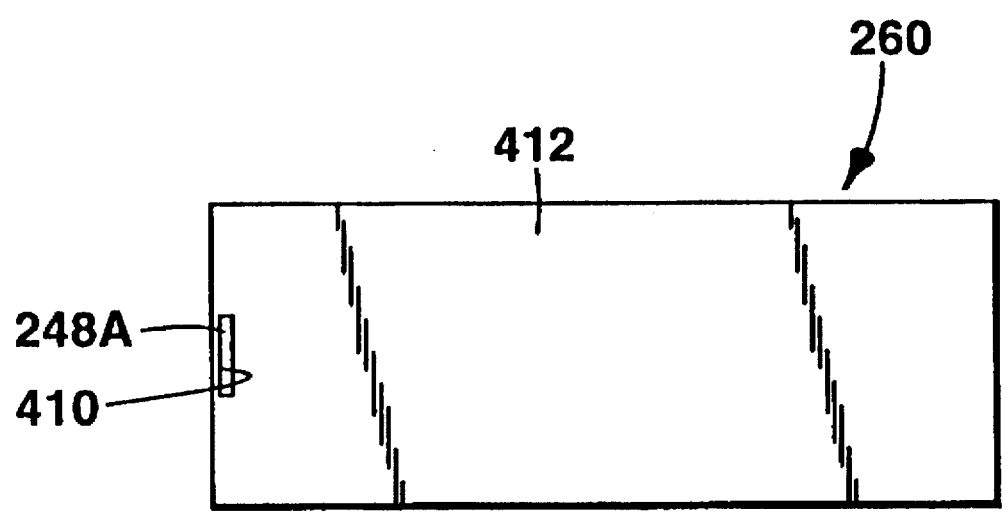
FIG. 28 is a side view of a container similar to the container of FIG. 24 showing a tab-holding slit through the opposite side walls of the container for holding a pouch in position in the container.
Figure 31:
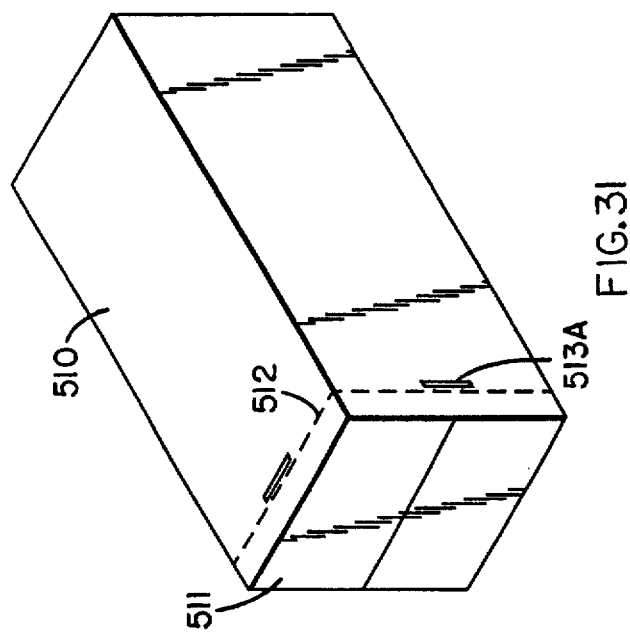
FIG. 31 is a perspective view of a container adapted to receive a pouch of the present invention.
Figure 30:
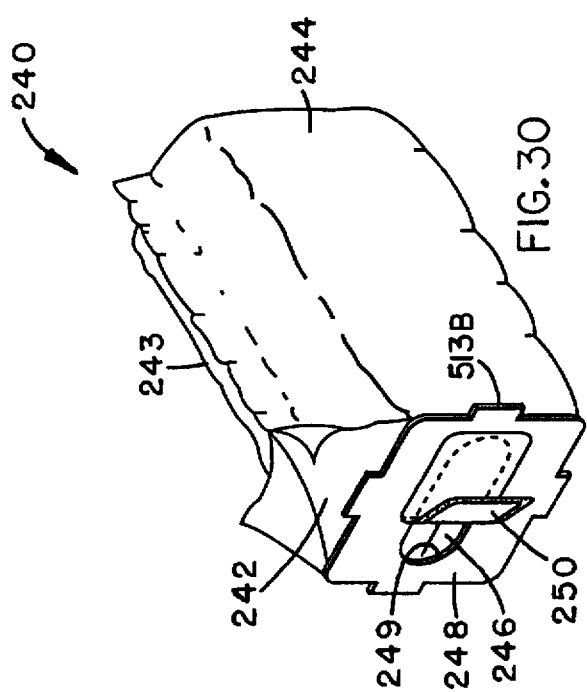
FIG. 30 is a perspective view of one preferred pouch according to the present invention, incorporating a frame surrounding an opening in the pouch.
Figure 29:
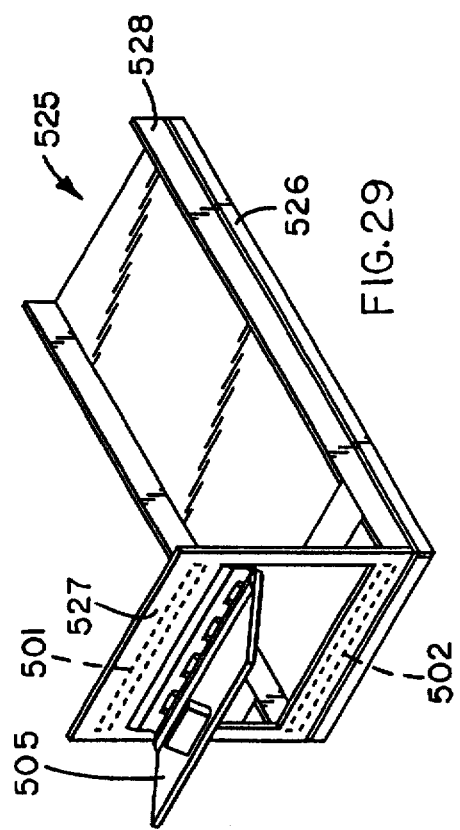
FIG. 29 is a perspective view of a dispenser adapted to receive a container which further contains a pouch of the present invention.
Figure 32:
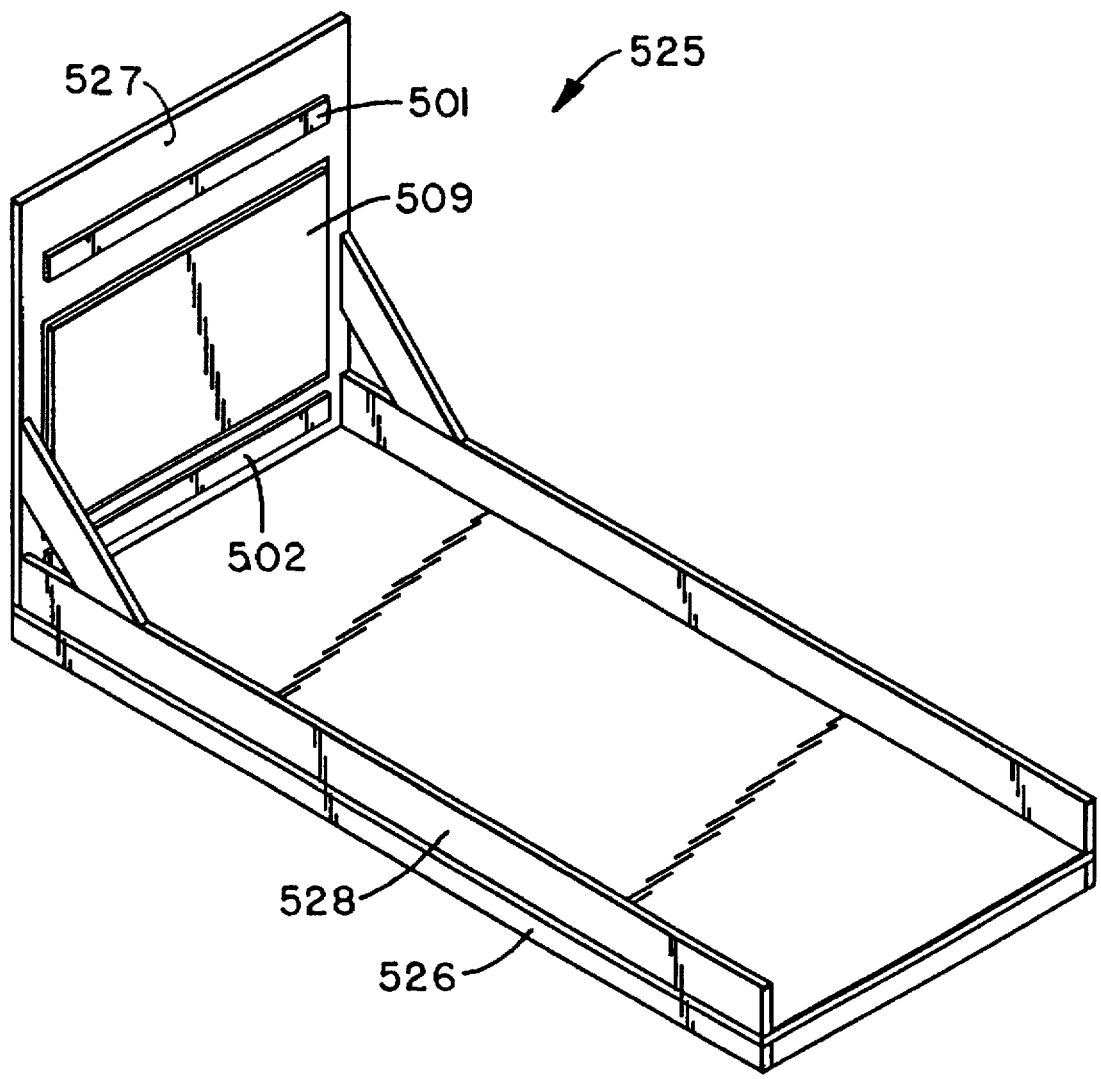
FIG. 32 is a perspective view of the dispenser of FIG. 29 rotated about 90° and showing a closed door.
Figure 33:
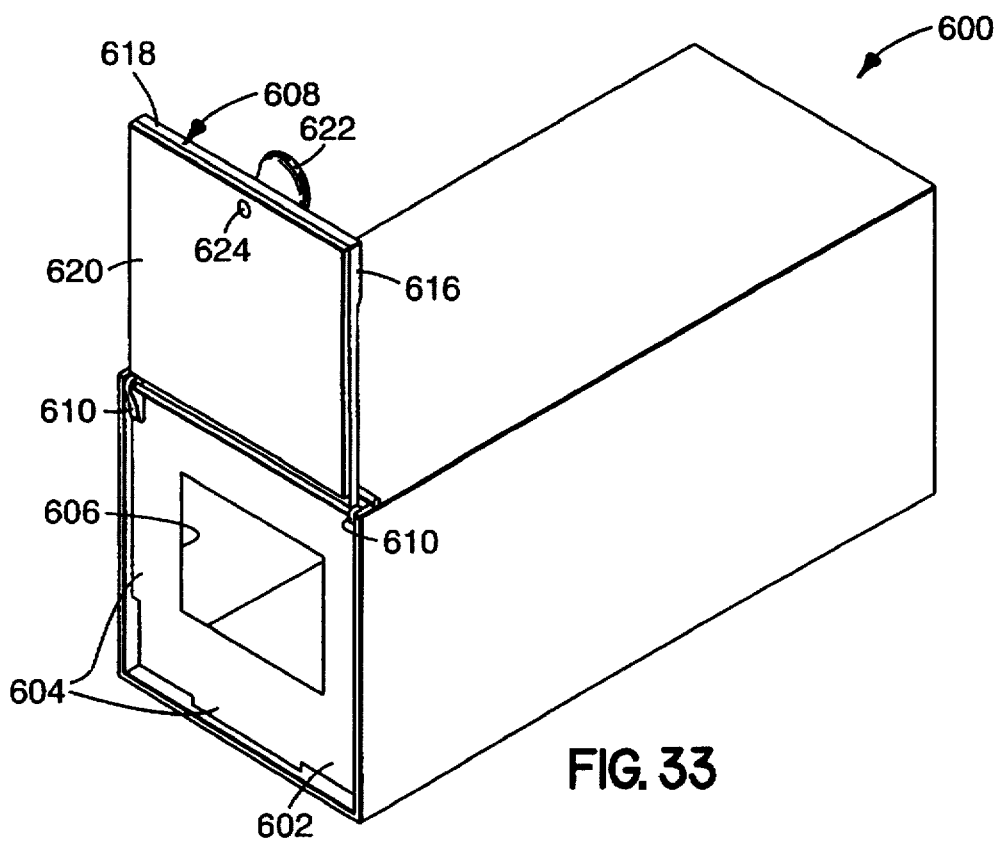
FIG. 33 is a perspective view of another preferred embodiment of a container of the invention, illustrating a novel door in its open position.
Figure 34:
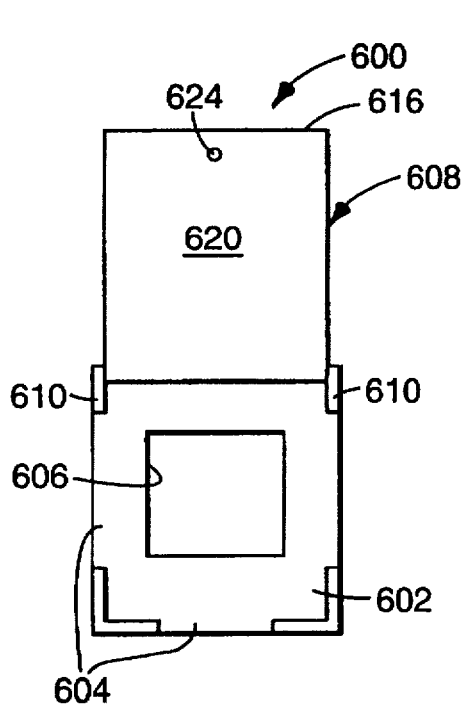
FIG. 34 is frontal view of the container of FIG. 33.
Figure 35:
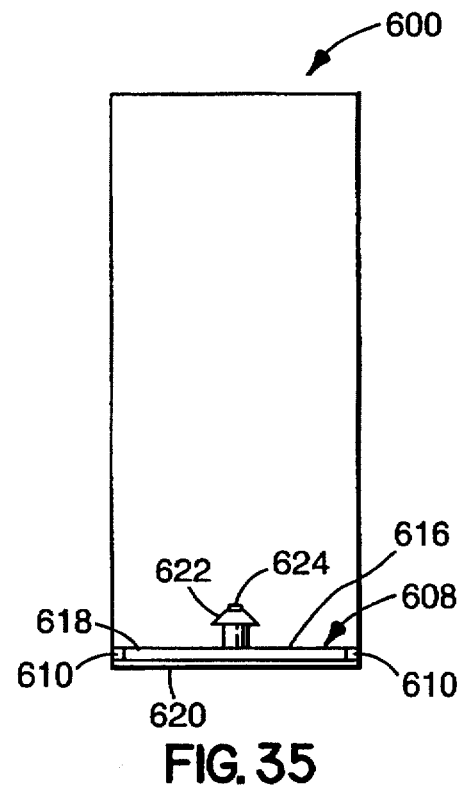
FIG. 35 is a top plan view of the container of FIGS. 33 and 34.
Figure 36:
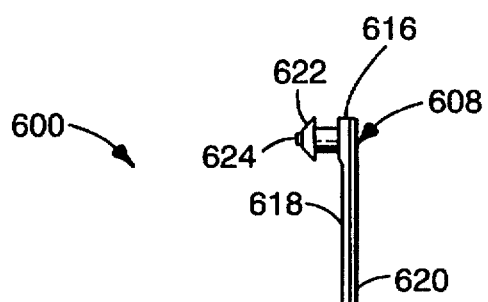
FIG. 36 is a left side elevation of the container of FIGS. 33–35.
Figure 37:
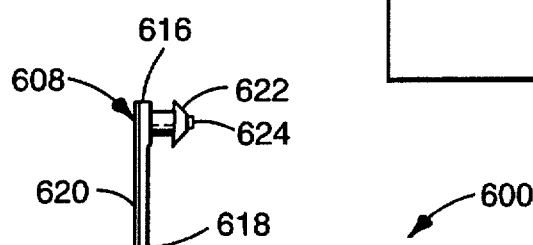
FIG. 37 is a right side elevation of the container of FIGS. 33–36.
Figure 38:
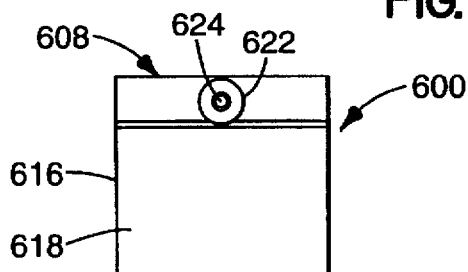
FIG. 38 is a rear view of the container of FIGS. 33–37.
Figure 39:
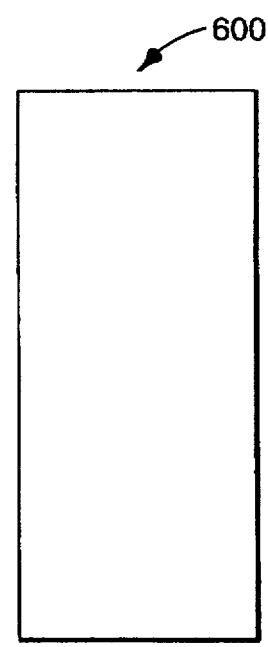
FIG. 39 is a bottom plan view of the container of FIGS. 33–38.
Figure 40:
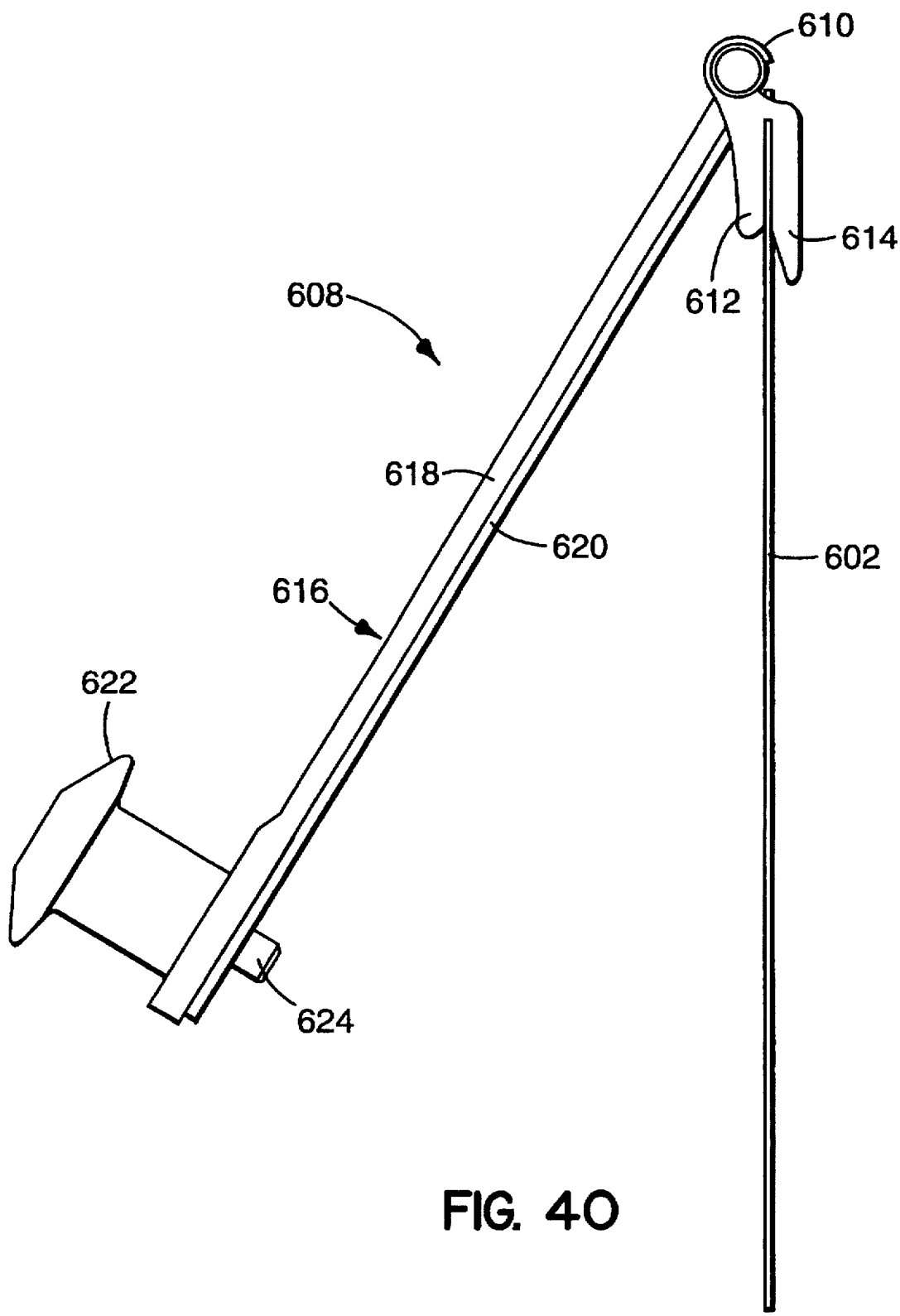
FIG. 40 is a side view of the door assembly for the container of FIGS. 33–39 mounted on a metal plate-like frame of a pouch.

An alternative securing means, which may be used with tabs 248A or opposite frame edges, comprises opposite slits or slots 410 cut through the opposite side walls 412 as illustrated in FIG. 28, to securely receive the tabs 248A or opposite frame edges to hold the frame 248 against the front end of the container 260 in alignment with the opening 263 and door 262. The slits or slots 410 may be cut only partly through the side walls 412 as opposed to completely through as shown in FIG. 28.

Door 262 provides means for access to the interior of the container 260 which contains pouch 240. Although door 262 is depicted as hinged it will be understood that many other means of providing access to the frame 248 of pouch 240 contained in container 260 could be provided. Examples could include simply removing a portion of the container 260 to provide access to the frame 248 and pouch 240 contained therein.

In the preferred embodiment, a remanently magnetized magnet sheet 266 is attached to the inner surface of the door 262. The preferred magnet sheet 266 is formed of a remanently magnetized material such as available under the trade designation "PLASTIFORM™ -B1033", from Arnold Engineering, Inc., Norfolk, Nebr., which also provides the required moisture impermeability to seal the opening 246 in pouch 240 when the door 262 is closed.

The magnet sheet 266 can be attached to door 262 by a variety of means such as adhesives, mechanical fasteners, hook and loop materials, etc. The preferred method of attachment involves the use of a sheet 264 of non-remanently magnetized material. The most preferred non-remanently magnetized material is 1010 steel (sheet metal) which is adhesively bonded to the door 262. As such, the magnetic attraction between magnetic sheet 266 and sheet metal 264 retains magnetic sheet 266 on door 262. Because the magnet sheet 266 has a larger amount of surface area in contact with sheet 264 than with frame 248 when door 262 is closed, it is retained on door 262 when opened rather than remaining attached to frame 248 (due to the stronger magnetic attraction).

The use of separate magnet sheet 266 as described for the preferred embodiment is advantageous in that the magnet sheet 266 can be reused after container 260 and associated pouch 240 are discarded, thereby reducing packaging waste and cost. Also, if a sheet 264 is used in combination with magnetic sheet 266, both pieces could be removably attached to door 262 for reuse with other containers 260 and pouches 240. Alternatively, magnet sheet 266 could be bonded directly to door 262, in which case the sheet 264 described above is unnecessary.

It is the arrangement of door 262, magnet sheet 266, and frame 248 which provides the magnetic means for providing a moisture-proof seal over the opening 246 in pouch 240. When door 262 is closed, the attraction between magnetic sheet 266 and frame 248 provides a moisture-proof seal for preventing premature curing of moisture-curable products contained in pouch 240. It will be understood that if the magnet sheet 266 is not itself moisture impervious, then either the door 262 or sheet 264 must be moisture impervious and the bonds between those materials and the magnet sheet 266 must also be moisture impervious.

Many alternate embodiments of the magnetic sealing mechanism could be provided. Magnet sheet 266 could be formed with a void in its center which mirrors the void 249 in frame 248. In that embodiment, the magnet sheet 266 would preferably be bonded to the door 262 to prevent it from being retained on the frame 248 when door 262 was opened. Furthermore, the sheet 264 (if present) or the door 262 itself would have to be moisture-impervious to provide a sufficient seal over the opening 246 in pouch 240. In addition, any bonds between the magnet sheet 266 and the moisture impervious material would also have to be moisture proof.

Other embodiments of the magnetic means for providing a moisture proof seal over opening 246 could include a frame 248 formed of remanently magnetized material which could be used to seal with a moisture impervious sheet 264, or door 262 which could itself be either non-remanently magnetized or remanently magnetized as desired to provide the required magnetic attraction to seal opening 246.

Figure 23:
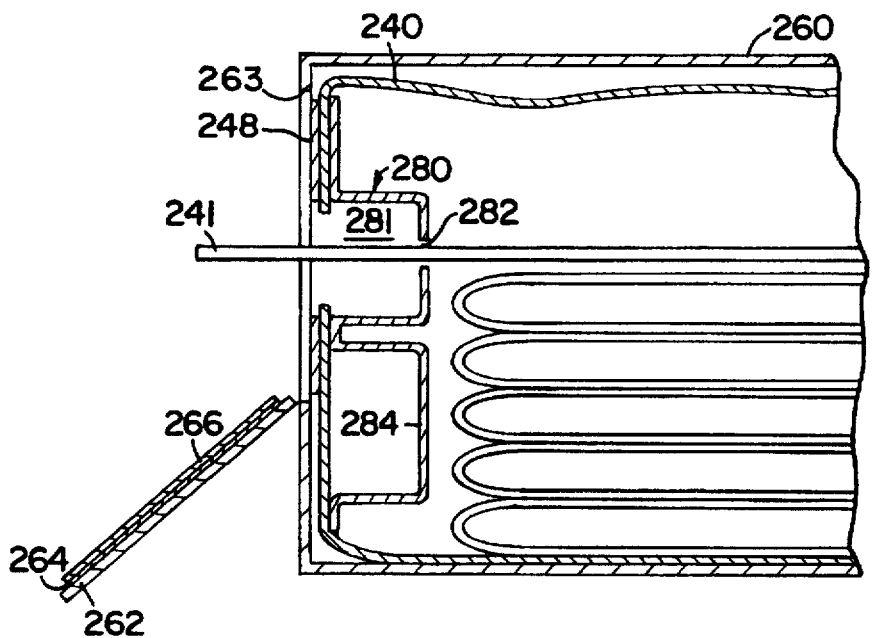
FIG. 23 is a perspective cross-section along line 23—23 of the combination of FIG. 22.

Also in the preferred embodiment, pouch 240 includes retaining means disposed within the pouch 240 for retaining the moisture-curable orthopedic splinting/casting product proximate the opening 246 of pouch 240. In the preferred embodiment the retaining means comprises a tray or other insert 280 which is disposed opposite the frame 248 as depicted in FIG. 23. Insert 280 is preferably adhesively bonded to the inner surface of the pouch 240.

Insert 280 includes a slot 282 formed therein through which the splinting/casting product 241 is threaded to reach opening 246 in pouch 240. It will be understood that the dimensions of slot 282 can be varied to provide friction and/or compression between the product 241 and slot 282 which will retain product 241 within slot 282. Slot 280 can also be provided with serrated edges to further prevent the product 241 from falling back into pouch 240. In the preferred embodiment, product 241 is threaded through slot 282 when delivered to a customer to simplify removal.

Also in the preferred embodiment, slot 282 is located a distance from opening 246 as shown in FIG. 23 to create a staging space 281 between the void 249 in frame 248 and the slot 282. The staging space 281 provides an area for storage of product 241 which has been pulled through slot 282 but not yet dispensed. As such, the additional product 241 can be forced back into the area between slot 282 and frame 248 for storage when door 262 is closed.

Furthermore, it will be understood that frame 248 and insert 280 could be formed integrally of a single material which could then be bonded to an opening 246 in the pouch 240. One example of such an embodiment could be formed of stamped sheet metal which would provide the desired magnetic properties needed to ensure a moisture proof magnetic seal over the opening 246.

The insert 280 of the preferred embodiment also preferably includes spacing means to prevent the product 241 from moving underneath slot 282. If the product does move under the slot 282, the force required to pull the product 241 through slot 282 can be increased beyond desired levels. The preferred spacing means comprises a stand-off 284 as shown in FIG. 23 which merely prevents the product 241 from sliding underneath slot 282. It will be understood that many other means of preventing the product 241 from sliding underneath slot 282 could also be provided and the preferred means disclosed herein is only one version of such devices.

As depicted in FIG. 23, the preferred retaining means and spacing means are both provided in the insert 280. Although the stand-off 284 is shown as forming a second cavity in addition to staging area 281, it will be understood that staging area 281 could be extended downward to encompass the standoff 284. In either situation, the insert 280 provides the desired functions of both retaining the product 241 proximate the opening and preventing the stored product from moving underneath slot 282.

In the preferred embodiment, insert 280 is constructed of a thermoformed material which presents sufficient rigidity to accomplish the functions described above.

FIG. 24 depicts an alternate preferred embodiment of a magnetic sealing closure for use with pouches constructed according to the preferred invention. As depicted in FIG. 24, the pouch 240 is supplied in a container 290 from which one panel is removed. The removed panel can be on a side or end of the container 290 as desired.

As depicted in FIG. 24, this preferred embodiment includes a structure 292 adapted to fit within the container 290. Structure 292 includes an opening 294 which receives and retains the frame 248 attached to pouch 240. Also attached to structure 292 is a door 296 which can be hinged or, alternatively, can be unconnected to the structure 292. Door 296 includes magnetic material 298 which is used to seal the opening 246 in frame 248 of pouch 240 in the same manner as described with respect to container 260 and its associated components described above. If the magnet material 298 itself does not provide the necessary moisture barrier, door 296 can be constructed of a moisture-impervious material to prevent premature curing of the product 241 contained within pouch 240. An advantage of the structure 292 is the simplification of the container 290 needed to hold the pouch 240 during dispensing, as the components of the seal are all reusable, with the exception of the frame 248 attached to pouch 240.

It will also be understood that the closure designs illustrated in FIGS. 16-19 and described above could also be adapted for use with the preferred pouches such as pouch 240 and any container in which pouch 240 was provided, in much the same way as structure 292 is described above.

Referring to FIGS. 16 & 17 for example, the addition of a remanently magnetized strip along the lower surface of base plate 202 would allow closure 200 to be used to reseal pouch 240. With the addition of the magnet to the lower surface of base plate 202, closure 200 would be magnetically sealed to the frame 248 of pouch 240. Lower extension 212 of closure 200 could be sized to fit within pouch 240 through opening 246. In the alternative, the lower surface of base plate 202 could include a non-remanently magnetized strip which could be attached to frame 248 if the frame 248 were provided of a remanently magnetized material as described above.

Referring to FIGS. 18 & 19, the addition of a remanently magnetized strip along the lower surface of base plate 222 would allow closure 220 to be used to reseal pouch 240. With the addition of the magnet to the lower surface of base plate 222, closure 220 would be magnetically sealed to the frame 248 of pouch 240. In the alternative, the lower surface of base plate 222 could include a non-remanently magnetized strip which could be attached to frame 248 if it were provided of a remanently magnetized material as described above.

Figure 25:
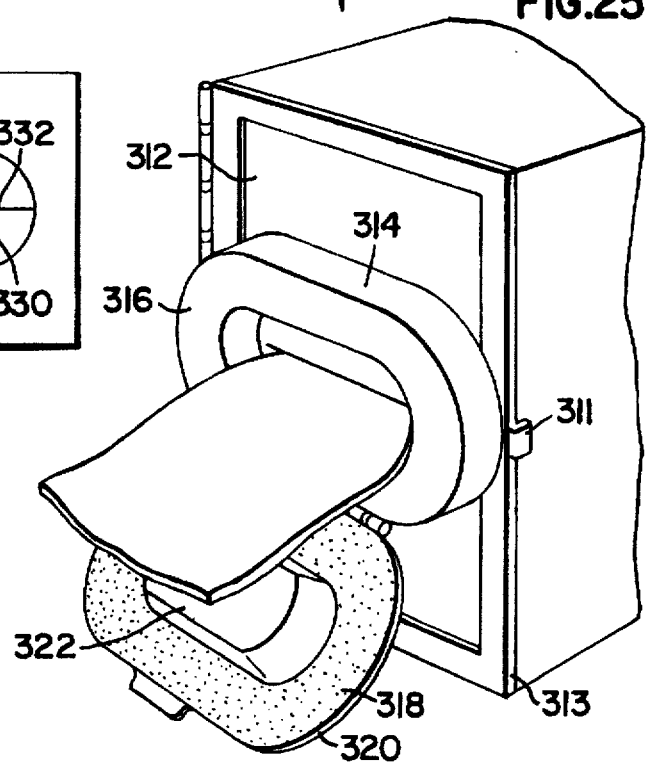
FIG. 25 is a perspective view of an alternative combination according to the present invention, the combination including a container and a pouch.

FIG. 25 depicts yet another alternate preferred embodiment of a pouch 240 which is disposed within a container 310 which includes a hinged door 312 which includes a latch 311 to retain door 312 closed after a pouch 240 has been placed within container 310. Containers such as 310 are preferably supplied as reusable containers in which pouches 240 are placed to dispense their product.

Door 312 preferably has a magnetic attachment on its inner surface (not shown) which mates with the frame 248 on pouch 240. Channel 314 extends outward from frame 248 and has a second magnetic sealing system on its distal end which includes surface 316 and corresponding surface 318 on the door 320. At least one of the surfaces 316 and 318 is remanently magnetized with the opposing surface being either remanently magnetized or non-remanently magnetizable. Door 320 is preferably hinged to channel 314, although it could be unconnected to channel 314 and retained in place by magnetic attraction between surfaces 316 and 318.

As such, the door 320 can be closed and magnetically sealed and frame 248 is also magnetically sealed to the inner surface of door 312. As a result, both magnetic seals combine to provide magnetic means for providing a moisture-proof seal over the opening 246 in pouch 240.

Door 320 also preferably includes a cupped portion 322 formed on its inner surface within magnet 318 which fits within channel 314 when door 320 is closed. The cupped portion 322 provides a means for guiding excess product back into the channel 314 as door 320 is closed and also helps to protect the magnet 318 from debris formed when the product is cut as it is being dispensed.

Alternatively, it will be understood that frame 248 could be provided of a non-magnetic material in the embodiment depicted in FIG. 25, provided that door 312 of container 310 is itself sealed to prevent moisture penetration of pouch 240. In that embodiment, any means of affixing frame 248 to the inner surface of door 312 could be provided. The magnetic sealing necessary to prevent moisture penetration into pouch 240 would be provided the magnetic sealing necessary using surfaces 316 and 318 on door 320.

Figure 26:
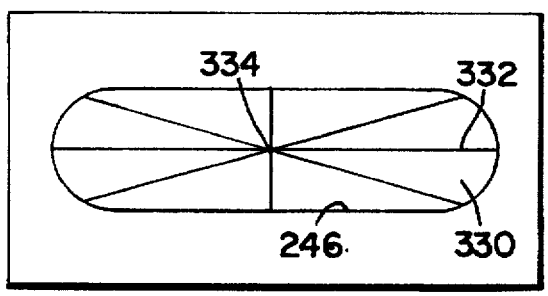
FIG. 26 is a view of the preferred supplemental sealing means for use with pouches according to the present invention.

An additional supplemental sealing means is illustrated in FIG. 26. As depicted, the preferred supplemental sealing means comprises a diaphragm 330 formed of a resilient material disposed over the opening 246 in pouch 240. The diaphragm 330 preferably includes radial slits 332 through the diaphragm 330 which extend from the center 334 of the diaphragm 330 to the periphery of opening 246. The preferred resilient material used for diaphragm 330 is neoprene or a similar resilient material which can provide some level of resealing if a cover is not immediately replaced to seal opening 246 in pouch 240.

It will also be understood that the diaphragm 330 could be attached to the door 312 or in the channel 314 of container 310 depicted in FIG. 25. It could also be attached to the structure 292 depicted in FIG. 24 or to either of closures 200 or 220 depicted in FIGS. 16–19.

FIGS. 29–32 depict yet an additional preferred embodiment of a pouch used to store moisture-curable orthopedic splinting/casting products and a container used to store the pouch for shipping and dispensing of the products in the pouch. Referring to FIGS. 29 to 32, pouch 240 is contained in an outer container 510 which can be used for shipping pouch 240 as well as containing pouch 240 during dispensing of a product from pouch 240. Preferred container 510 is formed of corrugated cardboard and is designed to be discarded with pouch 240 after the product is removed. Outer container 510 has an end panel 511 positioned so that the panel 511 can be removed (e.g., torn off) thereby exposing frame 248 of an enclosed pouch 240. The end panel 511 can be removed, for example, by incorporating a tear strip 512 circumferentially around the box near the end of the box, by scoring perforations around the box near the end of the box, by printing a line around the box which serves as a pattern to guide a knife, or by any other suitable means to separate the end panel from the major portion of the box thereby exposing frame 248. Tear strip 512 is preferably positioned near the end of the container 510 such that when the tear strip is circumferentially torn around the perimeter of the box and end panel 511 is detached, the frame 248 is exposed and aligned nearly flush with the remaining major portion of container 510.

In use, tear strip 512 is employed to separate the end panel 511 from container 510 thereby exposing frame 248. Adhesive sealing tape 250 is then removed from opening 246. Outer container 510 containing pouch 240 and exposed frame 248 is then slid into dispenser 525. In a preferred embodiment dispenser 525 comprises support portion 526 connected to a sealing portion 527. Sealing portion 527 has a door 505 with a remanently magnetized magnet sheet 509 attached to the inner surface of the door 505 as well as remanently magnetized magnet strips 501 and 502 positioned above and below or alternatively around door 505 on the inside of sealing portion 527. If desired, frame 248 can be oversized, i.e., have a larger surface area than that of the door 505. In use, outer container 510 with frame 248 exposed (i.e., end panel 511 is detached) and adhesive sealing tape 250 removed is placed in dispenser 525 and slid forward until magnet strips 501 and 502 magnetically bond to the oversized portion of frame 248. Alternatively, other means such as screws, clamps, tongue-and-groove type attachments or snap fit devices may be utilized to secure frame 248 to sealing portion 527. Magnet sheet 509 attached to the inner surface of door 505 hermetically seals opening 246 to prevent moisture vapor from prematurely curing splinting or casting material contained within the pouch 240.

Alternatively, after removal of end panel 511 the frame 248 may be recessed within the remaining major portion of container 510 or may protrude past the edge of the remaining major portion of container 510. If the frame 248 is recessed within the remaining major portion of container 510, it will be necessary to adapt sealing portion 527 to extend inside the recess and thereby cause magnet sheet 509 to seal opening 246.

In a preferred embodiment, frame 248 contains tabs 513b which engage slots 513a cut into outer container 510. Preferably, slots 513a are positioned at the edge of the remaining major portion of container 510 and align frame 248 flush with said edge.

Support portion 526 helps provide support to outer container 510 and helps maintain the aligned relationship between outer container 510 and sealing portion 527. Support portion 526 may optionally contain a ledge (not shown) similar to side walls 528. The ledge is preferably positioned a suitable distance away from the sealing portion 527 to thereby create a space which provides a tight fit with the remaining major portion of container 510. Thus, the optional ledge and remaining major portion of container 510 mechanically press the frame 248 against the sealing portion 527.

FIGS. 33–41 illustrate yet another preferred embodiment of the container of the invention, herein designated in its entirety by the reference numeral 600. The container 600 constitutes a corrugated cardboard box 600 housing a pouch similar to pouch 240. The pouch includes a steel plate-like frame 602 having tabs 604 similar to the tabs 513B of the frame of pouch 240, and an opening 606 through which moisture curable orthopedic casting or splinting materials are dispensed.

A novel door assembly 608 is mounted on the frame 602 by means of two hinges 610. Each hinge 610 includes two legs 612 and 614 that frictionally receive a portion of the plate-like frame 602 between the legs 612 and 614 to hold the door assembly 608 on the pouch. The arrangement is such that the door assembly 608 can be reused, and the pouch and container 600 are disposable when their contents are used up. Each hinge 610 is extruded of aluminum material and cut to size. Alternatively, the hinges 610 and door assembly 608 could be injection molded of thermoplastic material.

The door assembly 608 also includes a door 616 comprising an extruded aluminum main body 618 having a remanently magnetized magnet sheet 620 adhesively bonded thereto. The aluminum main body 618 and hinges 610 are preferably provided with a clear anodized finish.

A knob 622 is provided on the door 616 to facilitate pivoting the door 616 to its open position. The knob 622 includes a release plunger 624 adapted to be manually pressed against the plate-like frame 602 to release the magnet 620 from the frame 602. The release plunger 624 has an enlarged middle section that is received in an axial passageway through the knob 622 to allow axial motion of the plunger 624 within a limited range of motion. The enlarged middle section of the plunger 624 is held captive between the magnet sheet 620 and the outer end of the knob 622 where the axial passageway has a reduced cross section. The outer end 626 of the plunger 624 is manually pressed to axially move the plunger 624 to release the magnet 620 of the door 616 from the plate-like frame 602. Most preferably, each of the enlarged middle section and end portions of the plunger 624 generally cylindrical, with shoulders formed between the middle section and the end portions to retain the plunger 624 within the passageway of the knob 622.

The knob 622 is preferably press fit into the main body 618 of the door 616 but may be attached by other suitable means, such as by welding or adhesive. The knob 622 is preferably formed of aluminum.

The hinges 610 may be joined together to ensure that they are aligned during connection or disconnection of the hinges 610 to the plate-like frame 602.

Figure 41:
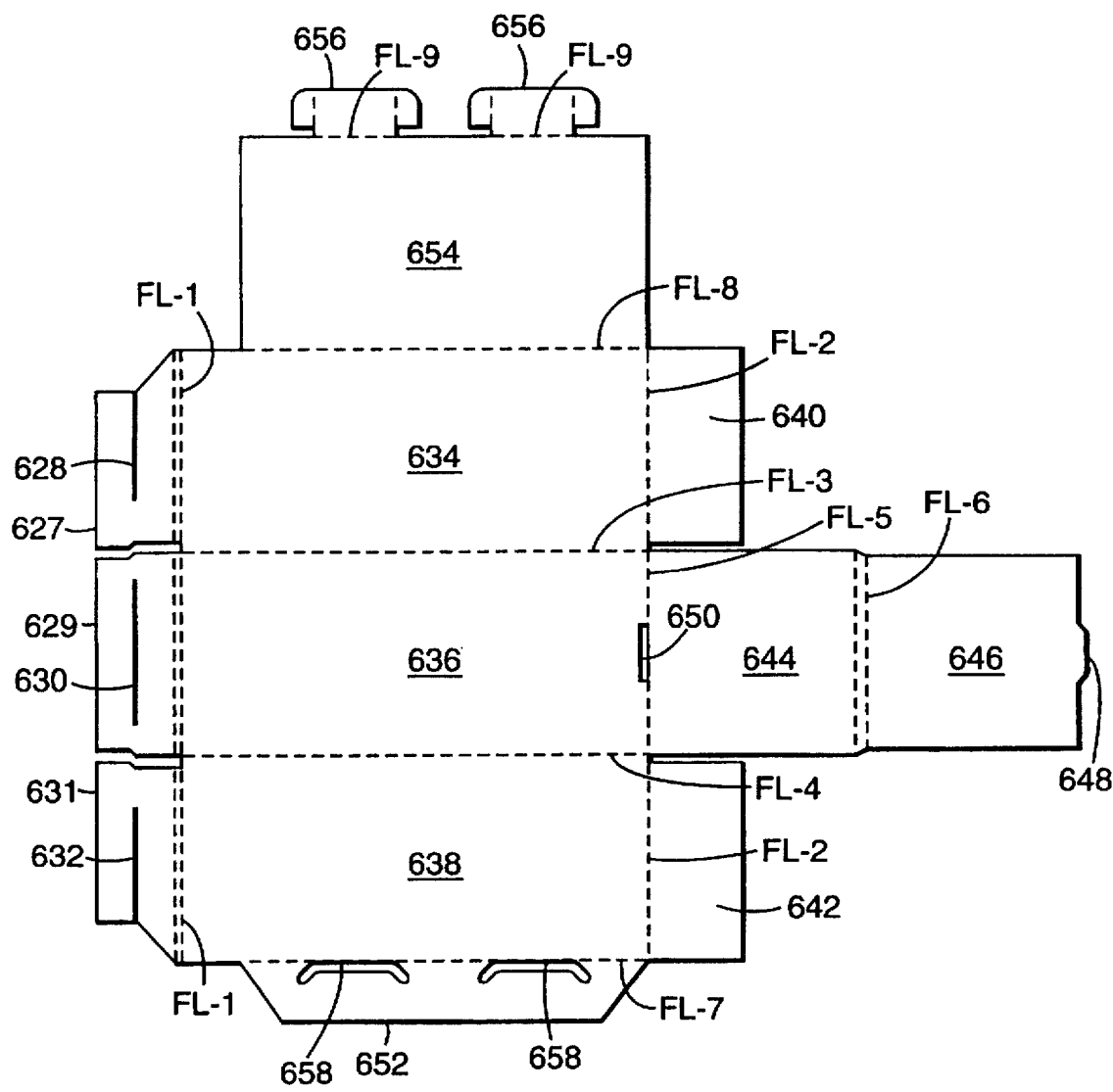
FIG. 41 is a plan view of a sheet of material cut but not yet folded to later form the container of FIGS. 33–40.

FIG. 41 is a plan view of the cardboard of the container 600 after it has been cut but before it has been folded to form the container 600. The cardboard is consecutively folded along fold lines FL-1, FL-2, FL-3, FL-4, FL-5, FL-6 and FL-7 to form the container 600.

Flaps 627, 629, 631 are first folded back along fold line FL-1 and glued to the main panels 634, 636 and 638 of the container 600. Slots 628, 630 and 632 in flaps 627, 629 and 631 are adapted to receive the tabs 604 of the plate-like frame 602.

Flaps 640 and 642 are then folded along fold line FL-2, and main panels 634 and 638 folded along fold lines FL-3 and FL-4 such that the flaps 640 and 642 are generally perpendicular to the main panels 634 and 638 and the main panels 634 and 638 are generally parallel to one another and each are generally perpendicular to the bottom main panel 636. Rear panels 644 and 646 are then folded along lines FL-5 and FL-6 and the tab 648 of rear panel 646 is inserted in the slot 650 to form the rear end of the container 600. Flap 652 is then folded along line FL-7 relative to the side main panel 638, and top panel 654 is folded along line FL-8 relative to the side main panel 634. Retaining tabs 656 on the top panel 654 are then folded along fold lines FL-9 relative to the top panel 654 and inserted into the slots 658 in flap 652.

Figures 42, 44:
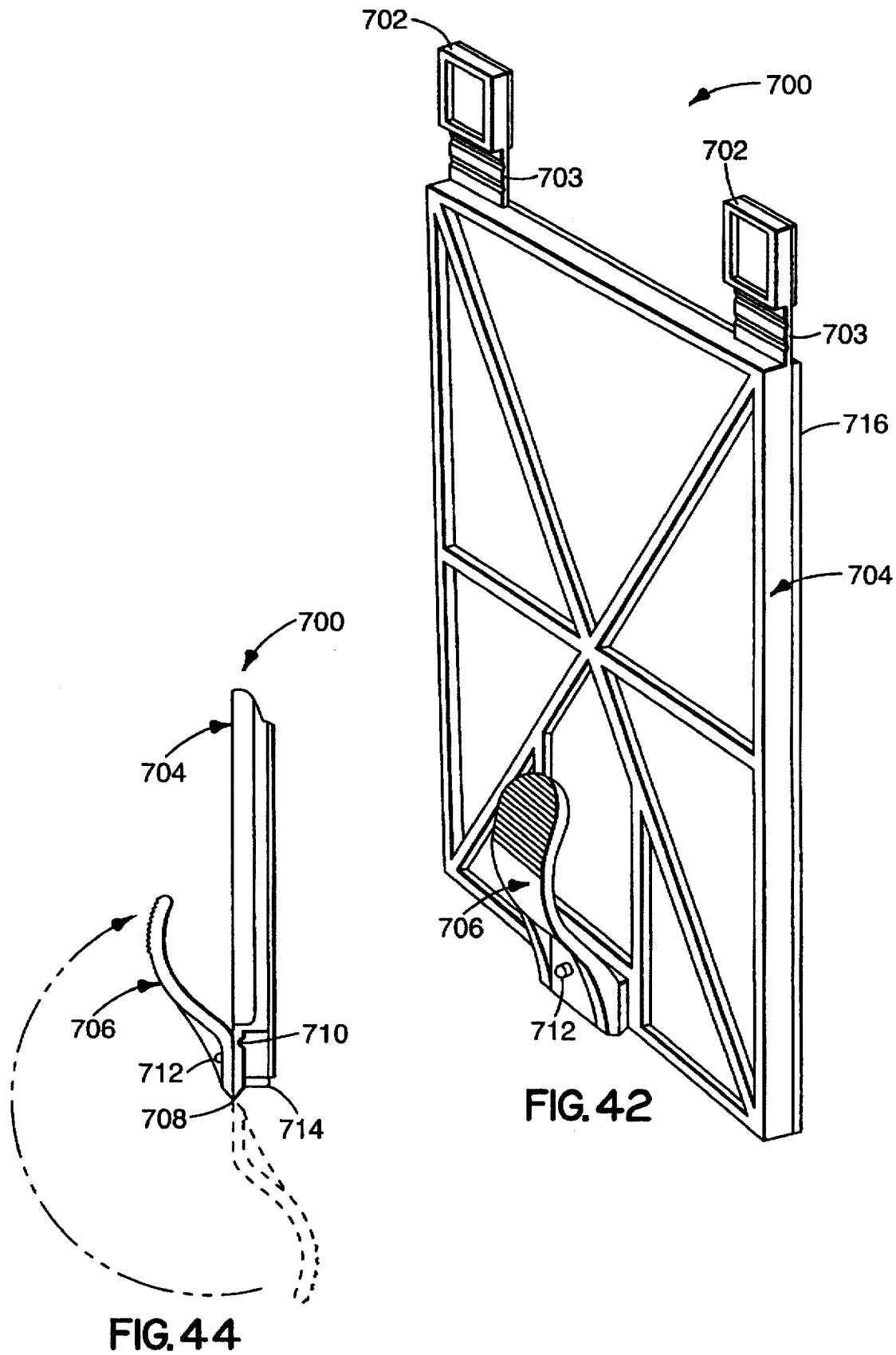
FIG. 42 is a perspective view of an alternative preferred embodiment of a door assembly for use with the container of FIGS. 33–39 and 41.
FIG. 44 is a partial side view of the door of FIGS. 42 and 43 illustrating a lever for releasing the magnet of the door from a metal plate-like frame of the pouch.
Figure 43:
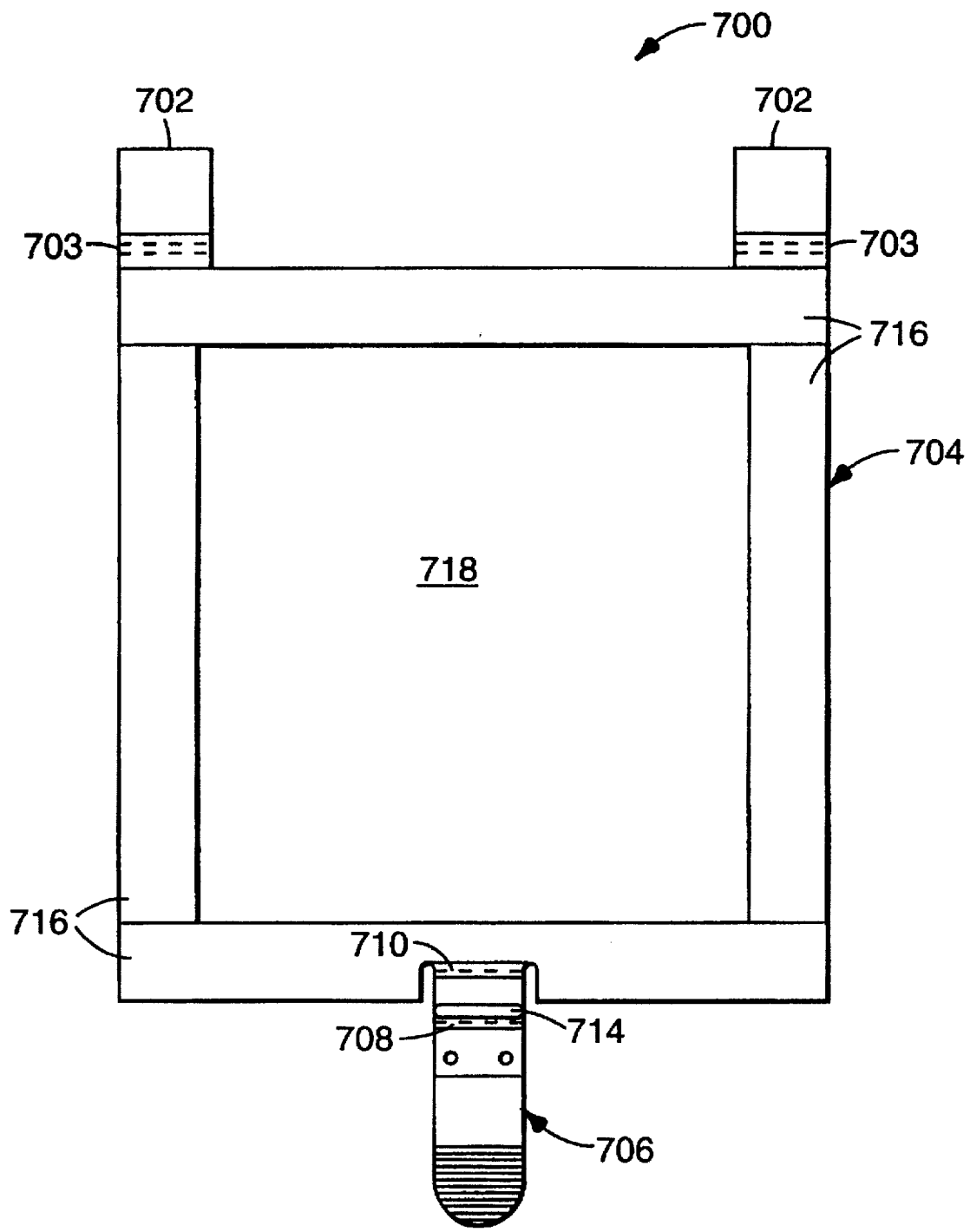
FIG. 43 is a back side view of the door of FIG. 42.

FIGS. 42-44 illustrate yet another alternative preferred embodiment of a door assembly of the invention herein designated 700. The door assembly 700 is preferably injection molded of thermoplastic material, such as high density polyethylene or polytetrafluoroethylene. The door assembly 700 includes a door 704 and tabs 702 connected by means of living hinges 703 to the door. The tabs 702 have a pressure sensitive adhesive layer for bonding the door assembly 700 to the plate-like frame of the pouch.

The door assembly 700 includes a door 704 and a release lever 706 connected to the door 700 by means of two living hinges 708 and 710. As best illustrated in FIG. 44, living hinge 708 allows the release lever 706 to be folded over against the door 704 from its original as molded position shown in phantom such that a suitable snap-fit type catch 712 holds the lever 706 in position.

Living hinge 710 allows the release lever 706 to be pivoted relative to the door 704 such that a projection 714 on the lever 706 engages the plate-like frame of the pouch to release the magnet strips 716 of the door 704 from the plate-like frame of the pouch. The release lever 706 is preferably provided with a surface texture, such as ridges, facilitating handling the release lever 706.

The door 704, tabs 702, living hinges 703, release lever 706, living hinges 708 and 710 and projection 714 are preferably integrally molded of the plastic material. As used herein integrally molded refers to integrally molded in one-piece as opposed to several pieces that have been fastened or bonded together.

The door 704 further includes a closed cell foam gasket 718 surrounded on four sides by the magnet strips 718. The magnet strips 718 are adhesively bonded to the main plastic body of the door 704 adjacent each edge of the door 704, and the gasket 718 is adhesively bonded to the main plastic body of the door 704 to provide an additional seal against the plate-like frame of the pouch when the door 704 is closed.

It is contemplated that the door assembly 700 would be a disposable part supplied with a container similar to container 600.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

We claim:

1. The combination of moisture-curable orthopedic splinting/casting product in a moisture-impervious, hermetically resealable pouch, the combination comprising:
    a) a pouch;
    b) a moisture-curable orthopedic casting/splinting product in the pouch;
    c) an opening in the pouch allowing access to the orthopedic casting/splinting product contained therein, the opening having first and second sides; and
    d) magnetic sealing means proximate the opening for hermetically resealing the opening, the magnetic sealing means comprising:
        1) a first magnet strip proximate a first side of the package, the first magnet strip having first and second ends;
        2) a second magnetic strip proximate a second side of the package, the second magnetic strip having first and second ends and, further, the second magnetic strip being magnetically attracted to the first magnet strip over substantially its entire length to bias the package in a closed position; and
        3) non-magnetic means for non-magnetically retaining the first end of the first magnet strip proximate the first end of the second magnetic strip and the second end of the first magnet strip proximate the second end of the second magnetic strip, the non-magnetic means comprising a pair of end caps, each end cap receiving and retaining a pair of ends of the first magnet strip and second magnetic strip in close relationship to each other.

2. The combination of claim 1, wherein the second magnetic strip is a remanently magnetized magnet strip.

3. The combination of claim 1, wherein the second magnetic strip is a non-remanently magnetizable strip.

4. The combination of claim 1, wherein the first magnet strip is attached to the first side of the opening and the second magnetic strip is attached to the second side of the opening.

5. The combination of claim 1, further comprising a backing strip attached to the first magnet strip.

6. The combination of claim 5, wherein the backing strip comprises an elongated strip of spring steel.

7. The combination of claim 1, further comprising a strip of stiffening material bonded to each of the first and second sides of the opening, the strips of stiffening material preventing wrinkling or puckering of the first and second sides of the opening when opened and closed.

8. The combination of claim 1, wherein the pouch comprises a main storage area and a sleeve extending from the main storage area, further wherein the opening is located in the sleeve.

9. The combination of claim 8, wherein the sleeve has a base proximate the main storage area of the pouch and an aperture distal from the pouch, the aperture having a width greater than the width of the sleeve at the base, the aperture width being within the range of 1.25 to 2.0 times greater than the base width.

10. The combination of claim 9, wherein the aperture width is within the range of 1.33 to 1.5 times greater than the base width.

11. The combination of claim 1, further comprising guiding means for guiding the moisture-curable orthopedic casting/splinting product towards the opening of the pouch, the guiding means comprising at least one heat seal extending into the pouch.

12. The combination of claim 1, wherein the moisture-curable orthopedic casting/splinting product further comprises an elongate water-curable splint.

13. The combination of claim 12, wherein the water-curable splint contains an isocyanate-curable resin.

14. The combination of claim 1, wherein the moisture-curable orthopedic casting/splinting product further comprises a plurality of individual rolls of water-curable resin impregnated sheets.

15. The combination of claim 14, wherein each of the plurality of individual rolls is individually packaged.

16. The combination of claim 1, further comprising a substantially rigid container substantially enclosing the pouch, the container allowing access to the opening of the pouch.

17. The combination of claim 16, further comprising compression means within the container for compressing the pouch as the moisture-curable orthopedic casting/splinting product is removed from it.

18. The combination of claim 17, wherein the compression means further comprises compressed foam which expands as the moisture-curable orthopedic casting/splinting product is removed from the pouch.

19. The combination of claim 1, wherein the pouch is constructed of a substantially flexible moisture-impervious material.

20. The combination of claim 19, wherein the substantially flexible material is a laminate comprising a metallic foil and plastic.

21. The combination of claim 19, wherein the pouch comprises a gusset.

22. The combination of moisture-curable orthopedic splinting/casting product in a moisture-impervious, hermetically resealable pouch, the combination comprising:

a) a pouch constructed of a substantially flexible moisture-impervious material comprising a laminate of metallic foil and plastic, the pouch comprising a main storage area and a sleeve extending from the main storage area;

b) a substantially rigid container substantially enclosing the pouch, the container allowing access to the pouch;

c) a moisture-curable orthopedic casting/splinting product containing an isocyanate-curable resin in the pouch;

d) an opening in the sleeve allowing access to the orthopedic casting/splinting product contained therein, the sleeve having first and second sides; and e) magnetic sealing means proximate the opening for hermetically sealing the opening, the magnetic sealing means comprising:

1) a first magnet strip proximate a first side of the package, the first magnet strip having first and second ends;

2) a second magnetic strip proximate a second side of the package, the second magnetic strip having first and second ends and, further, the second magnetic strip being magnetically attracted to the first magnet strip over substantially its entire length to bias the package in a closed position; and 3) non-magnetic means for non-magnetically retaining the first end of the first magnet strip proximate the first end of the second magnetic strip and the second end of the first magnet strip proximate the second end of the second magnetic strip, the non-magnetic means comprising a pair of end caps, each end cap receiving and retaining a pair of ends of the first magnet strip and second magnetic strip in close relationship to each other.

* * * * *